US011138515B2

(12) United States Patent
Shibahara

(10) Patent No.: US 11,138,515 B2
(45) Date of Patent: Oct. 5, 2021

(54) DATA ANALYSIS DEVICE, DATA ANALYSIS METHOD, AND RECORDING MEDIUM

(71) Applicant: Hitachi, Ltd., Tokyo (JP)

(72) Inventor: Takuma Shibahara, Tokyo (JP)

(73) Assignee: Hitachi, Ltd., Tokyo (JP)

(*) Notice: Subject to any disclaimer, the term of this patent is extended or adjusted under 35 U.S.C. 154(b) by 1082 days.

(21) Appl. No.: 15/550,508

(22) PCT Filed: Sep. 30, 2015

(86) PCT No.: PCT/JP2015/077796
§ 371 (c)(1),
(2) Date: Aug. 11, 2017

(87) PCT Pub. No.: WO2016/132588
PCT Pub. Date: Aug. 25, 2016

(65) Prior Publication Data
US 2018/0032910 A1 Feb. 1, 2018

(30) Foreign Application Priority Data
Feb. 18, 2015 (JP) .............................. JP2015-029606

(51) Int. Cl.
*G06N 20/00* (2019.01)
*G16H 50/70* (2018.01)
*G06N 7/00* (2006.01)

(52) U.S. Cl.
CPC .............. *G06N 20/00* (2019.01); *G06N 7/00* (2013.01); *G16H 50/70* (2018.01)

(58) Field of Classification Search
CPC ........... G06N 20/00; G06N 7/00; G16H 50/70
See application file for complete search history.

(56) References Cited

U.S. PATENT DOCUMENTS

2007/0038659 A1 2/2007 Datar et al.
2014/0188893 A1* 7/2014 Kobayashi .......... G06F 16/9014
707/747

(Continued)

FOREIGN PATENT DOCUMENTS

JP 2013-33551 A 2/2013
JP 2014-203289 A 10/2014
WO WO 2007/022199 A2 2/2007

OTHER PUBLICATIONS

International Search Report (PCT/ISA/210) issued in PCT Application No. PCT/JP2015/077796 dated Dec. 15, 2015 with English translation (Two (2) pages).

(Continued)

*Primary Examiner* — Li B. Zhen
*Assistant Examiner* — Tewodros E Mengistu
(74) *Attorney, Agent, or Firm* — Crowell & Moring LLP

(57) ABSTRACT

A data analysis apparatus executes: acquiring a group of learning input data; setting a plurality of first hash functions; substituting each learning input data in each of the plurality of first hash functions to thereby calculate a plurality of first hash values; selecting, for the group of learning input data and for each of the plurality of first hash functions, a specific first hash value that satisfies a predetermined statistical condition from among the plurality of first hash values; setting a second hash function; substituting, for the group of learning input data, each specific first hash value in the second hash function to thereby calculate a plurality of second hash values; and generating a learning feature vector that indicates features of the group of learning input data by aggregating the plurality of second hash values corresponding to respective specific first hash values and obtained as a result of the calculation.

13 Claims, 17 Drawing Sheets

(56) References Cited

U.S. PATENT DOCUMENTS

| | | | |
|---|---|---|---|
| 2014/0304236 A1* | 10/2014 | Hachiya | G06K 9/6269 |
| | | | 707/687 |
| 2016/0078361 A1* | 3/2016 | Brueckner | H04L 67/10 |
| | | | 706/12 |
| 2016/0092267 A1* | 3/2016 | Boyacigiller | G06Q 10/0633 |
| | | | 718/103 |

OTHER PUBLICATIONS

Japanese-language Written Opinion (PCT/ISA/237) issued in PCT Application No. PCT/JP2015/077796 dated Dec. 15, 2015 (Three (3) pages).

Li, P., et al., "Theory and Application of b-Bit Minwise Hashing," ACM 54.8 (2011) (Nine (9) pages).

* cited by examiner

FIG. 5

352 PREDICTION DATA SET

510

| ID | SEX (i=1) 511 | AGE (i=2) 512 | DRUG A (i=3) 513 | DRUG B (i=4) 514 | ... | DRUG Ω (i=200,000) 515 |
|---|---|---|---|---|---|---|
| 1 | MALE | 50 | 2.5 mg | 1 mg | ... | - |
| 2 | FEMALE | 49 | - | - | ... | 0.25% |
| 3 | FEMALE | 22 | - | 3 mg | ... | ... |
| ... | ... | ... | ... | ... | ... | ... |
| N' = 100,000 | FEMALE | 31 | 7.0 mg | 3 mg | ... | 0.10% |

$D'_1, D'_2, D'_3, ..., D'_N$ → $D'$

500

520

| ID | PROSPECT OF REMISSION 521 | WBC 522 | RBC 523 | Lymphocyte 524 | ALT 525 |
|---|---|---|---|---|---|
| 1 | - | - | - | - | - |
| 2 | - | - | - | - | - |
| 3 | - | - | - | ... | - |
| ... | ... | ... | ... | ... | ... |
| N' = 100,000 | - | - | - | - | - |

$Y'_1, Y'_2, Y'_3, ..., Y'_N$ → $Y'$

500

DATA ANALYSIS DEVICE, DATA ANALYSIS METHOD, AND RECORDING MEDIUM

CLAIM OF PRIORITY

The present application claims priority from Japanese patent application JP 2015-029606 filed on Feb. 18, 2015, the content of which is hereby incorporated by reference into this application.

BACKGROUND OF THE INVENTION

This invention relates to a data analysis apparatus, a data analysis method, and a data analysis program, for analyzing data.

Hitherto, for example, there has been known a technology of checking whether or not a purchaser has made purchases for all the products stored in a database when identifying the type of the purchaser from purchase information of products to recommend a product. This classifies purchasers into groups having similar purchase tendencies. In that process, the number of product items reaches tens of thousands to hundreds of millions, and thus an enormous amount of time is required for a computer to simply check all the items.

In view of the above, a system of JP 2013-033551 A acquires an interest set for each of a plurality of users, determines M minimum hash values of the interest set for each user, and assigns each of the plurality of users to each of M clusters established for each user, to thereby perform recommendation and other operations.

When the system of JP 2013-033551 A uses K n-bit hash functions to generate a vector sequence having as its element a binary scalar value representing purchase information of a given user (for example, elements "0" and "1" thereof indicate "not purchased" and "purchased", respectively. The vector is hereinafter referred to as "feature vector"), the size of the feature vector results in D=2n(K/n) dimensions. In JP 2013-033551 A, when normal parameters (number K of hash functions and number n of bits being 100 and 32, respectively) are given, the number of dimensions of the feature vector results in 429,496,729,600 dimensions.

Further, in Li, Ping, and Arnd Christian König. "Theory and applications of b-bit minwise hashing." Communications of the ACM 54.8 (2011), there is proposed a technique of achieving dimension reduction by truncating the feature vector to lower b-bits. For example, when the feature vector in 429,496,729,600 dimensions, which is generated from the number K of hash functions and the number n of bits being 100 and 32, respectively, is truncated by b=2 bits, the size of a final feature vector results in 200 dimensions.

In JP 2013-033551 A, hash functions are used to determine M minimum hash values of an interest set. However, there is a problem in that the number of dimensions of the feature vector is enormous, and thus calculation processing is time consuming.

Further, in Li, Ping, and Arnd Christian König. "Theory and applications of b-bit minwise hashing." Communications of the ACM 54.8 (2011), the number of dimensions is reduced by truncating the feature vector to lower b-bits, and thus the calculation processing time is shortened compared with JP 2013-033551 A. However, there is a problem in that the analysis accuracy deteriorates due to b-bit truncation.

Further, for example, in order to analyze drug efficacy based on purchase information of, for example, a drug, not only an information item of two values for indicating whether or not there has been a purchase, but also an information item of multiple values or real values, such as the number of doses or a prescription amount of a drug, needs to be managed in some cases. However, none of JP 2013-033551 A and Li, Ping, and Arnd Christian König. "Theory and applications of b-bit minwise hashing." Communications of the ACM 54.8 (2011) considers generation of a feature vector in a case where the value of an item to be analyzed has multiple values or real values.

SUMMARY OF THE INVENTION

This invention has an object to achieve rapid and accurate data analysis.

An aspect of the invention disclosed in this application is a data analysis apparatus, which is executed by a processor capable of accessing a storage device, the processor being configured to execute: first acquisition processing of acquiring a group of learning input data, which is a set of learning input data that contains values of a plurality of first data items, from the storage device; first setting processing of setting a plurality of first hash functions by generating first hash tables, which are independent of one another; first calculation processing of substituting each learning input data of the group of learning input data acquired by the first acquisition processing in each of the plurality of first hash functions set by the first setting processing, to thereby calculate a plurality of first hash values corresponding to the values of the plurality of first data items for each of the plurality of first hash functions; first selection processing of selecting, for the group of learning input data and for each of the plurality of first hash functions, a specific first hash value that satisfies a predetermined statistical condition from among the plurality of first hash values, which have been calculated for each of the plurality of first hash functions by the first calculation processing; second setting processing of setting a second hash function by generating a second hash table; second calculation processing of substituting, for the group of learning input data, each specific first hash value, which has been selected for each of the plurality of first hash functions by the first selection processing, in the second hash function set by the second setting processing, to thereby calculate a plurality of second hash values; and first generation processing of generating a learning feature vector that indicates features of the group of learning input data by aggregating the plurality of second hash values corresponding to respective specific first hash values and obtained as a result of the calculation by the second calculation processing.

According to the representative embodiment of this invention, it is possible to achieve rapid and accurate data analysis. The details of one or more implementations of the subject matter described in the specification are set forth in the accompanying drawings and the description below. Other features, aspects, and advantages of the subject matter will become apparent from the description, the drawings, and the claims.

BRIEF DESCRIPTION OF THE DRAWINGS

FIG. 5 is an explanatory diagram for illustrating an example of the prediction data set.

DETAILED DESCRIPTION OF THE PREFERRED EMBODIMENTS

In the following, a description is given in detail of embodiments of this invention with reference to the drawings as necessary. Further, in the embodiments, a description is given using drug efficacy analysis as an example, but the drug efficacy analysis is only one example, and this invention is applied to various kinds of purposes such as product recommendation and analysis of a news article.

First Embodiment

Figure 1:
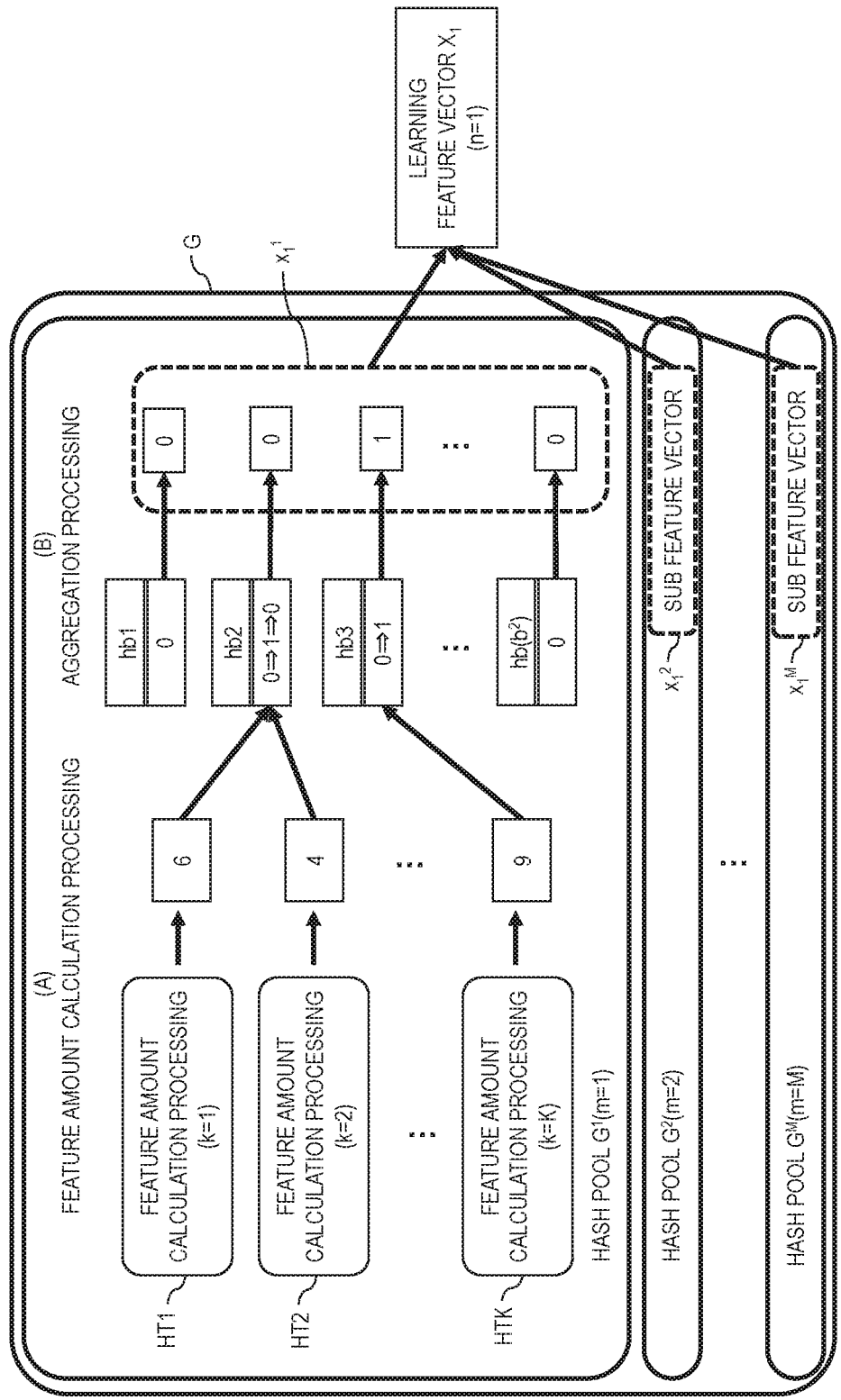
FIG. 1 is an explanatory diagram for illustrating an example of generation of a feature vector according to a first embodiment of this invention.

FIG. 1 is an explanatory diagram for illustrating an example of generation of a feature vector according to a first embodiment of this invention. When a known group of learning input data and learning output data are prepared, a feature vector can be generated. In the case of drug efficacy analysis, the group of learning input data is, for example, a group of learning factor data containing data items such as sex, age, and a prescription amount of a drug for each patient. Further, the group of learning output data is, for example, a group of learning diagnosis data containing data items such as prospect of remission, a white blood cell (WBC) count, a red blood cell (RBC) count, a lymphocyte count, and a liver function (ALT) test value for the same patient of the group of learning factor data. For example, information described in an electronic health record in a hospital or a medical prescription are used as the group of learning factor data and the group of learning diagnosis data.

When the group of learning factor data is denoted by D, each learning factor data of the group is represented by Expression (1) given below. When the group of learning diagnosis data is denoted by Y, each learning diagnosis data of the group is represented by Expression (2) given below.

$$D_n = \{x_n^i | i \in I\} \quad (1)$$

$$Y_n = \{y_n^p | p \in P\} \quad (2)$$

The symbol n represents identification information for identifying a patient on each data of the group of learning factor data D and the group of learning diagnosis data Y, where n=1, 2, ..., N. The symbol i represents identification information for identifying a data item such as sex (i=1), age (i=2), a prescription amount (i=3) of a drug A, and a prescription amount (i=4) of a drug B, where i=1, 2, ..., I. The symbol p represents identification information for identifying a data item such as the prospect of remission (p=1), the white blood cell count (p=2), and the red blood cell count (p=3) in the learning diagnosis data, where p=1, 2, ..., P.

Further, the learning feature vector is generated for each patient. The learning feature vector of an n-th patient is represented by $X_n$.

The learning feature vector $X_n$ is generated to obtain a learning parameter w common in patients for a diagnosis item (e.g., prospect of remission). Specifically, when each learning feature vector $X_n$ is generated, each learning feature vector $X_n$, the group of learning factor data D, and a learning diagnosis data sequence of each patient for a diagnosis item (e.g., prospect of remission) are used to execute machine learning, for example, support vector machines (SVM), to thereby calculate the learning parameter w. Then, the learning parameter w and a group of factor data (hereinafter referred to as "group of factor data for prediction") of another patient can be used to predict a diagnosis data sequence of another patient for a diagnosis item (e.g., prospect of remission).

In generation of the learning feature vector $X_n$, a hash pool family G is generated in advance. The hash pool family G is a set of hash pools $G^m$ as represented by Expression (3) given below.

$$G = \{G^m | m = 1, 2, ..., M\} \quad (3)$$

Each hash pool $G^m$ contains a plurality of hash functions. In the first embodiment, a description is given on the assumption that n=1 and m=1. However, the same processing is performed for n=2, ..., N, and m=2, ..., M.

(A) Feature amount calculation processing and (B) aggregation processing (odd-filtering) are executed for the hash pool $G^1$ to generate a feature vector $X_1$.

In (A) feature amount calculation processing, feature amount calculation processing HTk (k=1, 2, ..., K) is executed. The feature amount calculation processing HTk is processing of calculating feature amounts corresponding to values of respective data items of learning factor data $D_n$ from the learning factor data $D_n$ using a different hash function, and selecting a minimum value among those feature amounts.

The different hash functions may be hash functions having different hash algorithms, or may be hash functions having the same hash algorithm but internally storing different hash tables. The bit width of each hash value is the same (a-bit) among different hash functions. The symbol a represents an integer of one or more. The feature amount calculation processing HTk produces one minimum value for each patient.

In (B) aggregation processing, a hash function is used to aggregate the minimum values obtained in (A) feature amount calculation processing. In the first embodiment, the minimum values are aggregated by modular arithmetic using odd-filtering. The odd-filtering is processing of repeating flip of two values (0 and 1) serving as aggregated values. In this case, the aggregated value is set to two values, but may be set to three or more values. The hash function in this case has a hash value of b-bit width, and $b^2$ hash values are prepared and serve as respective aggregated values. The symbol b represents an integer of one or more.

For example, the minimum value "6" obtained in feature amount calculation processing HT1 using the learning factor data $D_1$ corresponds to a hash value hb2 among hash values hb1 to hb($b^2$) of a hash table generated by a b-bit hash function. Therefore, the aggregated value corresponding to the hash value hb2 flips from the initial value of "0" to "1". Next, the minimum value "4" obtained in the feature amount calculation processing HT2 using the learning factor data $D_1$ also corresponds to the hash value hb2. Therefore, the aggregated value corresponding to the hash value hb2 flips from "1" to "0".

As the value of b becomes smaller, the same hash value is more likely to be hit. In (B) aggregation processing, this property is used to aggregate minimum values obtained in (A) feature amount calculation processing.

In this manner, through completion of (B) aggregation processing, a sub feature vector $x_1^1$ that arranges the aggregated values of from the hash values hb1 to hb($b^2$) is generated. Sub feature vectors $x_1^2$ to $x_1^M$ are generated similarly for the hash pools $G^2$ to $G^m$. Then, through concatenation of the sub feature vectors $x_1^1$ to $x_1^M$, the feature vector $X_1$, which indicates features of the learning factor data $D_1$, is generated. Feature vectors $X_2$ to $X_N$, which indicate features of the learning factor data $D_2$ to $D_N$, are generated similarly for the learning factor data $D_2$ to $D_N$.

Figure 2:
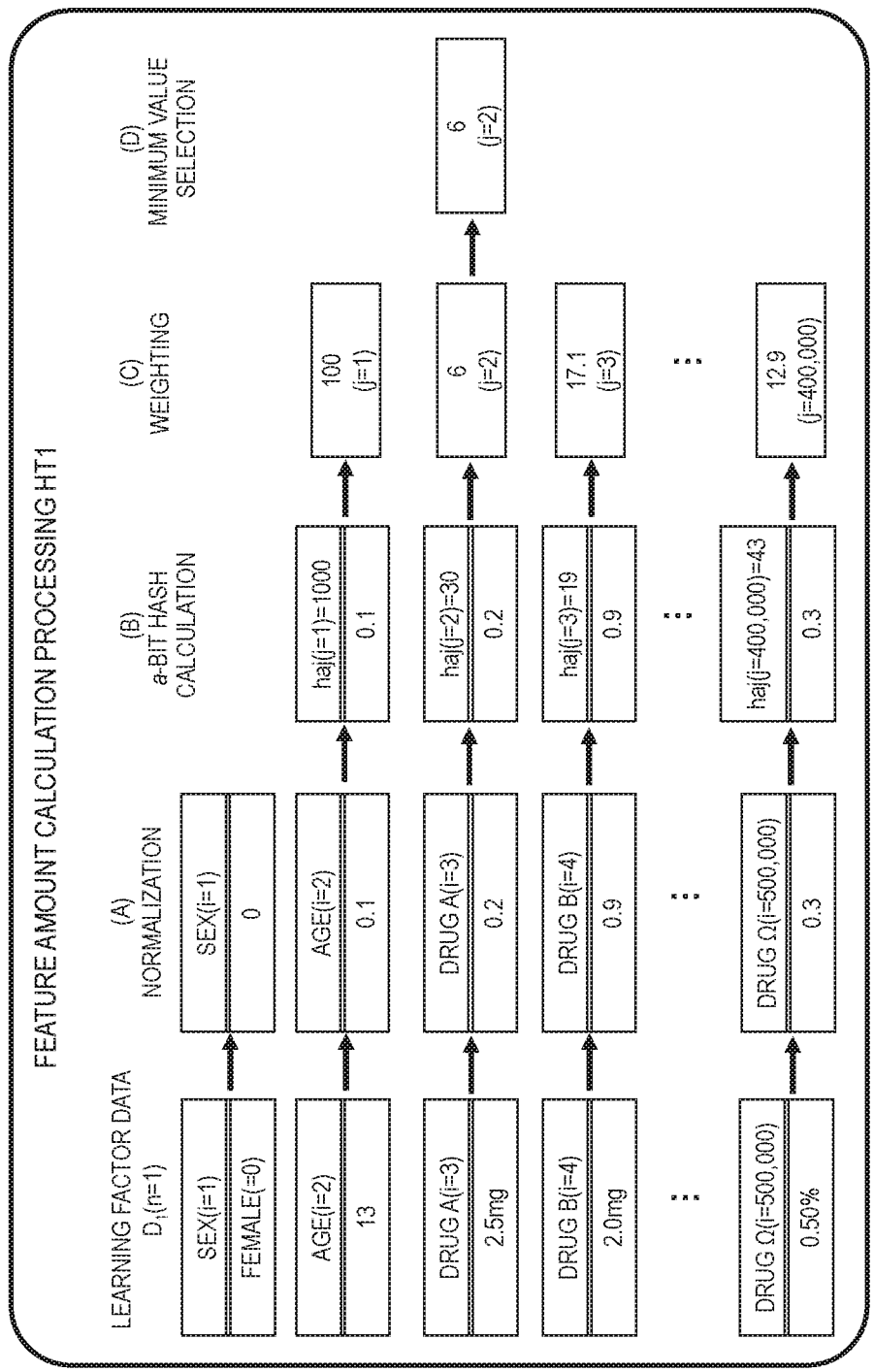
FIG. 2 is an explanatory diagram for illustrating in detail an example of processing of the feature amount calculation processing HT1 illustrated in FIG. 1.

FIG. 2 is an explanatory diagram for illustrating in detail an example of processing of the feature amount calculation processing HT1 illustrated in FIG. 1. In the feature amount calculation processing HT1, the minimum value is obtained from each learning factor data $D_n$, but the description given below is based on the assumption that n=1.

In the feature amount calculation processing HT1, when the learning factor data $D_1$ is given, (A) normalization, (B) a-bit hash calculation, (C) weighting, and (D) minimum value selection are executed. Unique identification information i (i=1, 2, . . . , N) is assigned to a data item such as sex, age, or the prescription amount of a drug of the learning factor data $D_1$. In FIG. 2, N=500,000 is set.

In (A) normalization, the value of a data item in the learning factor data $D_1$ is normalized. For example, in the case of a data item of multiple values, for example, "age", the maximum value and the minimum value of the data item are used for normalization such that the value becomes equal to or larger than 0 and equal to or smaller than 1.

Also in the case of a data item of real values, for example, "prescription amount of drug", the range that can be taken by the prescription amount of the drug is normalized such that the value becomes equal to or larger than 0 and equal to or smaller than 1. In the case of the data item of "sex", the possible value is, for example, two values of male (=1) and female (=0), and thus is used as it is without normalization.

In (B) a-bit hash calculation, a data item for which the value of the learning factor data $D_1$ before normalization is non-zero is selected. For example, when the value of the data item "sex" corresponding to i=1 is "female" (=0), the data item is not selected, whereas the value of "age" is "13", and thus the data item is selected. Data items for which values before normalization are selected are numbered again using j. In FIG. 2, for example, it is assumed that 400,000 data items are selected.

Then, in (B) a-bit hash calculation, a hash table generated by the a-bit hash function described above is used to associate the value after normalization of a data item for which the value before normalization is selected with a hash value haj corresponding to identification information on the data item for which the value before normalization is selected in the hash table.

For example, the value "0.1" after normalization of the data item "age" for which the value "13 (≠0)" before normalization is selected is associated with the hash value ha1 (=1,000) corresponding to identification information (j=1) on the data item "age" for which the value "13 (≠0)" before normalization is selected in the hash table.

In (C) weighting, the value after normalization and the corresponding hash value haj, which are associated with each other in (B) a-bit hash calculation, are multiplied.

In (D) minimum value selection, the minimum value is selected among a group of values obtained by (C) weighting. With this, the minimum value is obtained among feature amounts corresponding to values of respective data items of the learning factor data $D_1$ from the learning factor data $D_1$. In this description, the minimum value is selected, but other statistical values satisfying other statistical conditions, such as the maximum value, the median value, the average value, and a random value, may be selected.

In the feature amount calculation processing HT1 of FIG. 2, the description is given using the learning factor data $D_1$, but the feature amount calculation processing HT1 is executed similarly for the learning factor data $D_2$ to $D_N$. Further, in FIG. 2, the description is given using the feature amount calculation processing HT1, but the same processing is executed similarly for other feature amount calculation processing HT2 to HTK.

In this manner, in the first embodiment, an a-bit hash function is used to calculate the minimum value of feature amounts corresponding to values of respective data items of the learning factor data $D_n$ by the feature amount calculation processing HTk and aggregating the minimum values using a b-bit hash function. Therefore, it is possible to achieve more rapid data analysis.

Further, the normalized values of data items of the learning factor data $D_n$ are weighted by the a-bit hash function to obtain feature amounts, and the minimum values of those feature amounts are aggregated by odd-filtering to generate the learning feature vector $X_n$. Therefore, each element of the learning feature vector $X_n$ is a value that has taken two values, multiple values, and real values of each data item of the learning factor data $D_n$ into consideration. Therefore, it is possible to achieve more accurate data analysis.

Further, in the aggregation processing, values that can be taken by odd-filtering may be set small to achieve memory saving.

<System Configuration Example>

Figure 3:
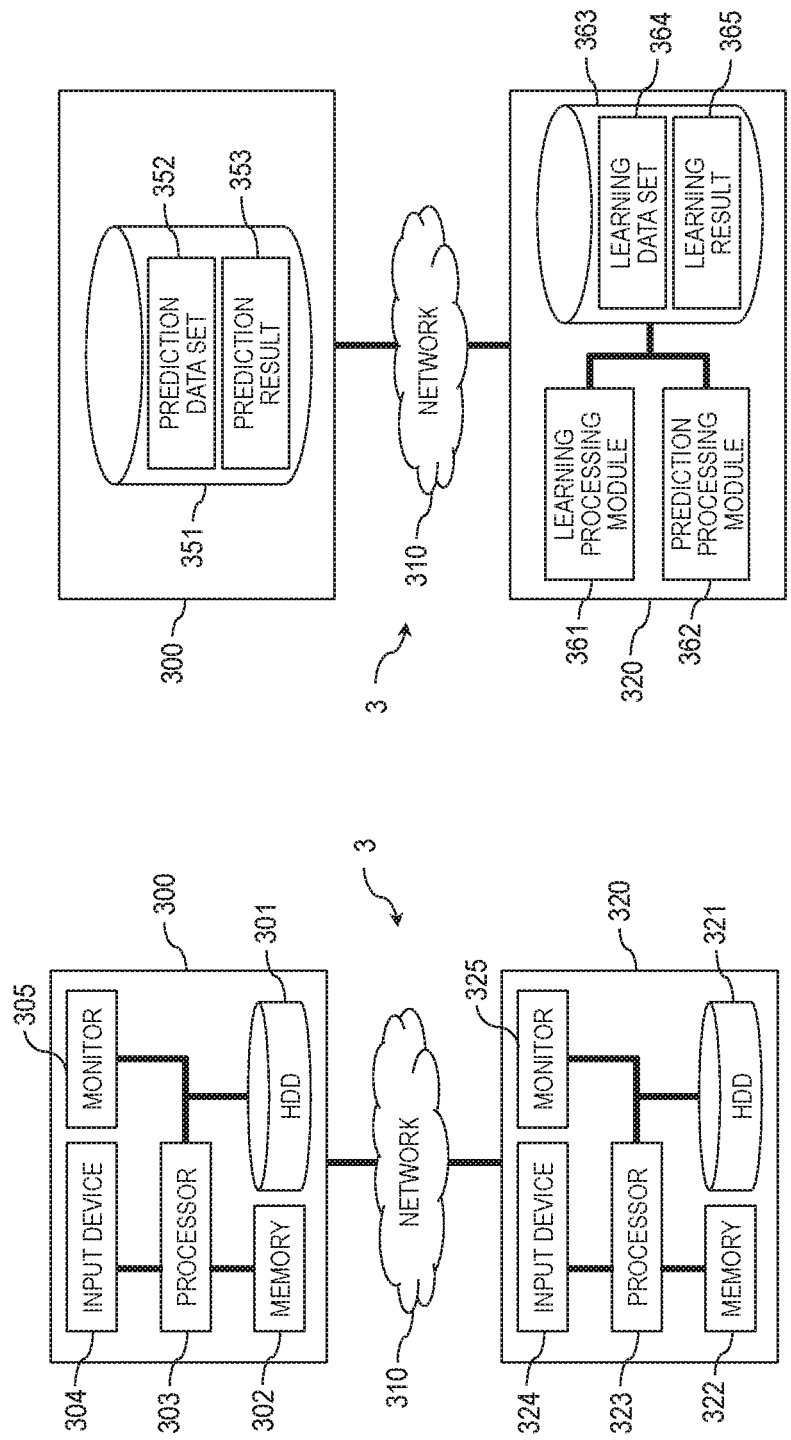
FIG. 3A is a block diagram for illustrating a hardware configuration example of the data analysis system.
FIG. 3B is a block diagram for illustrating a functional configuration example of the data analysis system.

FIG. 3A and FIG. 3B are each a block diagram for illustrating a system configuration example of a data analysis system 3. In FIG. 3A and FIG. 3B, a description is given using the client-server data analysis system 3 as an example, but the stand-alone data analysis system may also be used. FIG. 3A is a block diagram for illustrating a hardware configuration example of the data analysis system 3, and FIG. 3B is a block diagram for illustrating a functional configuration example of the data analysis system 3. In FIG. 3A and FIG. 3B, the same configuration is denoted by the same reference symbol.

The data analysis system 3 is configured such that a client terminal 300 and a data analysis apparatus 320, which is a server, are coupled to each other for communication via a network 310.

In FIG. 3A, the client terminal 300 includes a hard disk drive (HDD) 301, which is an auxiliary storage device, a memory 302, which is a main memory device, a processor 303, an input device 304, which is a keyboard or a mouse, and a monitor 305. The data analysis apparatus 320 includes an HDD 321, which is an auxiliary storage device, a memory 322, which is a main memory device, a processor 323, an input device 324, which is a keyboard or a mouse, and a monitor 325. The main memory device, the auxiliary storage device, and a portable storage medium (not shown) are hereinafter collectively referred to as "storage device".

In FIG. 3B, the client terminal 300 includes a client database (DB) 351. The client DB 351 is stored into storage devices such as the HDD 301 and the memory 302. The client DB 351 stores a prediction data set 352 and a prediction result 353. The prediction data set 352 is described later with reference to FIG. 5. The prediction result 353 is data acquired from a prediction processing module 362 via the network 310. In the case of a client-server data analysis system 3, there are one or more client terminals 300.

The data analysis apparatus 320 includes a learning processing module 361, the prediction processing module 362, and a server database (DB) 363. The learning processing module 361 is a functional module configured to execute the processing illustrated in FIG. 1 and FIG. 2 and output a learning result 365. The learning result 365 includes the learning parameter w described above. A processing procedure of the learning processing module 361 is described later in detail with reference to FIG. 7 to FIG. 9.

The prediction processing module 362 is a functional module configured to use the learning result 365 to execute the processing illustrated in FIG. 1 and FIG. 2 and output the prediction result 353 to the client terminal 300. A processing procedure of the prediction processing module 362 is described later in detail with reference to FIG. 7, FIG. 10, and FIG. 11. The learning processing module 361 and the prediction processing module 362 each cause the processor 323 to execute a program stored in the storage device such as the HDD 321 or the memory 322, to thereby implement the function.

The server DB 363 stores a learning data set 364 and the learning result 365. The learning data set 364 contains the group of learning input data (group of learning factor data D) and the group of learning output data (group of learning diagnosis data Y) described above. The learning result 365 is data output from the learning processing module 361.

The plurality of data analysis apparatus 320 may be used for configuration of the data analysis apparatus 320. For example, the plurality of data analysis apparatus 320 may be used for load balancing. Further, the plurality of data analysis apparatus 320 may be provided for respective functions. For example, a first server including the learning processing module 361 and the server DB 363 and a second server including the prediction processing module 362 and the server DB 363 may be used for configuration of the data analysis apparatus 320. Further, a first data analysis apparatus including the learning processing module 361 and the prediction processing module 362 and a second data analysis apparatus including the server DB 363 may be used for configuration of the data analysis apparatus 320. Further, a first server including the learning processing module 361, a second data analysis apparatus including the prediction processing module 362, and a third data analysis apparatus including the server DB 363 may be used for configuration of the data analysis apparatus 320.

<Learning Data Set>

Figure 4:
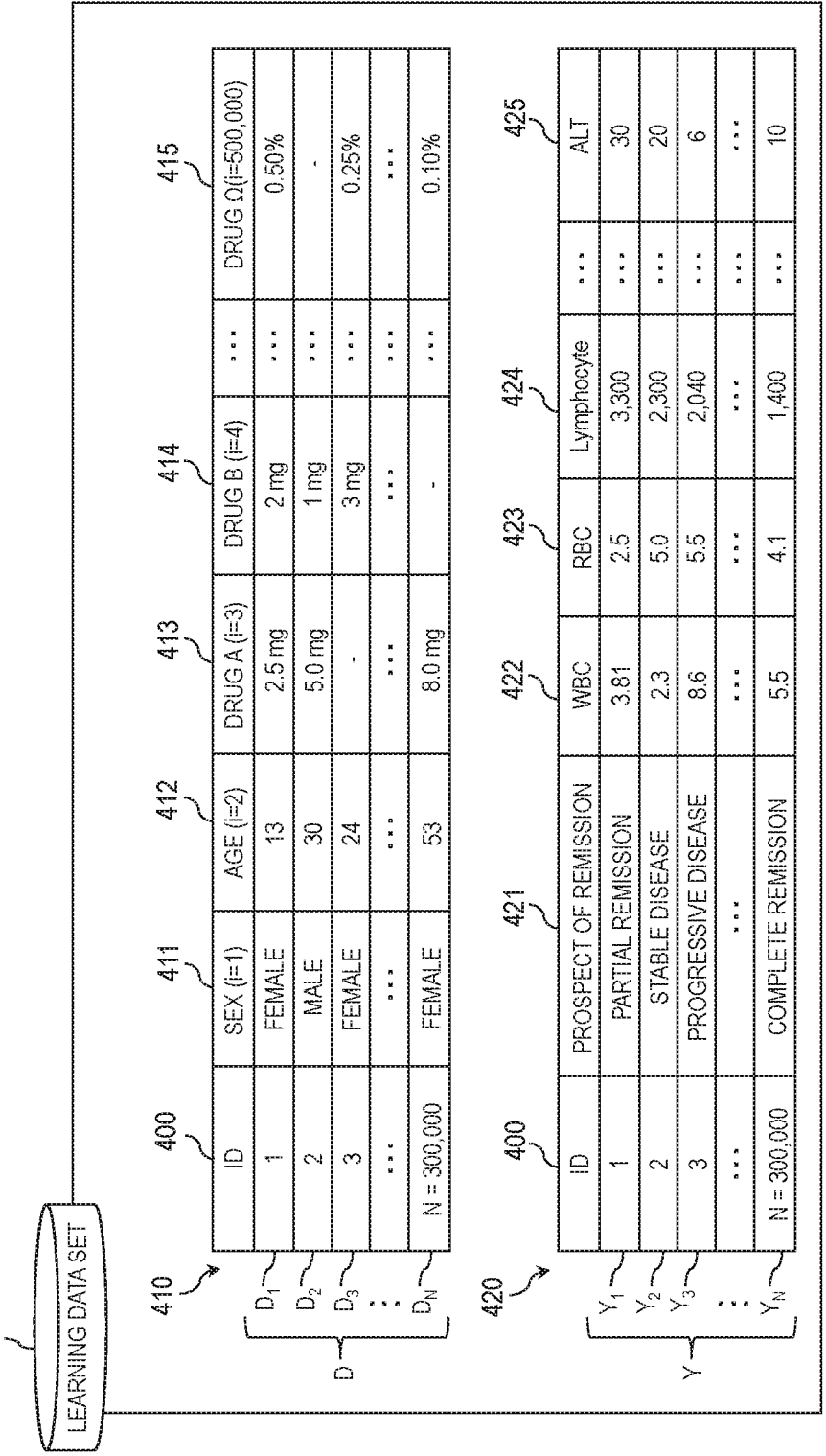
FIG. 4 is an explanatory diagram for illustrating an example of the learning data set.

FIG. 4 is an explanatory diagram for illustrating an example of the learning data set 364. The learning data set 364 includes a learning input DB 410 and a learning output DB 420. The learning input DB 410 is a database configured to store the group of learning input data (group of learning factor data D), and the learning output DB 420 is a database configured to store the group of learning output data (group of learning diagnosis data Y).

The learning input DB 410 includes, as data items, an ID 400, a sex (i=1) 411, an age (i=2) 412, a drug A (i=3) 413, a drug B (i=4) 414, . . . , and a drug Ω (i=500,000) 415, and a combination of values of those data items are used to construct the learning factor data $D_n$. In the first embodiment, the total number l of the data items i of the learning input DB 410 is set to l=500,000 as an example.

The ID 400 is a data item for storing, as a value, a numerical value n (=1, 2, . . . , N) for uniquely identifying a patient to be analyzed. The sex (i=1) 411 stores, as a value, a numerical value (e.g., "0" in the case of female and "1" in the case of male) for identifying sex of the patient n identified by the ID 400 through dummy variable generation processing. When the value of a data item takes multiple values of three or more, the data item is transformed into a data item using 1-of-K representation (e.g., only one out of K elements takes "1" and the others take "0").

The age (i=2) 412 is a data item for storing, as a value, the age of a patient identified by the numerical value n. The drug A (i=3) 413, the drug B (i=4) 414, . . . , and the drug Ω (i=500,000) 415 store, as values, prescription amounts (real numbers) of the drugs A, B, . . . , and Ω prescribed for the patient identified by the numerical value n.

The learning output DB 420 includes, as data items, prospect of remission (p=1) 421, a white blood cell count (p=2) 422, a red blood cell count (p=3) 423, a lymphocyte count (p=4) 424, . . . , and a liver function test value (p=P) 425, and a combination of values of those data items are used to construct learning diagnosis data $Y_n$.

The prospect of remission (p=1) 421 is a data item for storing, as a value, any one of four values, namely, progressive disease (=1), stable disease (=2), partial remission (=3), and complete remission (=4), for indicating the prospect of remission of a patient identified by the numerical value n. The white blood cell count (p=2) 422, the red blood cell count (p=3) 423, the lymphocyte count (p=4) 424, . . . , and the liver function test value (p=P) 425 are data items that store, as values, real values that correspond to those data items.

<Prediction Data Set>

FIG. 5 is an explanatory diagram for illustrating an example of the prediction data set. A prediction input DB 510 includes, as data items i, an ID 500, a sex (i=1) 511, an age (i=2) 512, a drug A (i=3) 513, a drug B (i=4) 514, . . . , and a drug Ω (i=200,000) 515, and a combination of values of those data items are used to construct prediction factor data $D'_{n'}$. In the first embodiment, the total number $I'$ of the data items i of the learning input DB 410 is set to $I'=200,000$ as an example.

$$D'_{n'}=\{x_{n'}{}^{i}|i\in I'\} \quad (4)$$

The symbol n' represents a numerical value (n'=1, 2, ..., N') for uniquely identifying a patient to be subjected to prediction. Further, the set of prediction factor data $D'_{n'}$ is set as a group of prediction factor data D'.

The ID 500 is a data item for storing, as a value, the numerical value n' (=1, 2, ..., N'). The value of the ID 500 is different from that of the ID 400. In other words, the patient identified by the ID 500 and the patient identified by the ID 400 are different patients. The sex (i=1) 511 stores, as a value, a numerical value (e.g., "0" in the case of female and "1" in the case of male) for identifying sex of n' identified by the ID 500 through dummy variable generation processing. When the value of a data item takes multiple values of three or more, the data item is transformed into a data item using 1-of-K representation (e.g., only one out of K elements takes "1" and the others take "0").

The age (i=2) 512 is a data item for storing, as a value, the age of a patient identified by the numerical value n'. The drug A (i=3) 513, the drug B (i=4) 514, ..., and the drug Ω (i=200,000) 515 store, as values, prescription amounts (real numbers) of the drugs A, B, ..., and Ω prescribed for the patient identified by the numerical value n'.

A learning output DB 520 includes, as data items, prospect of remission 521, a white blood cell count 522, a red blood cell count 523, a lymphocyte count 524, ..., and a liver function test value 525.

The values of the data items 521 to 525 are obtained by prediction, and thus do not store values. The client terminal 300 stores the prediction result 353 from the prediction processing module 362 of the data analysis apparatus 320 into the data items 521 to 525.

<Setting Screen Example>

Figure 6:
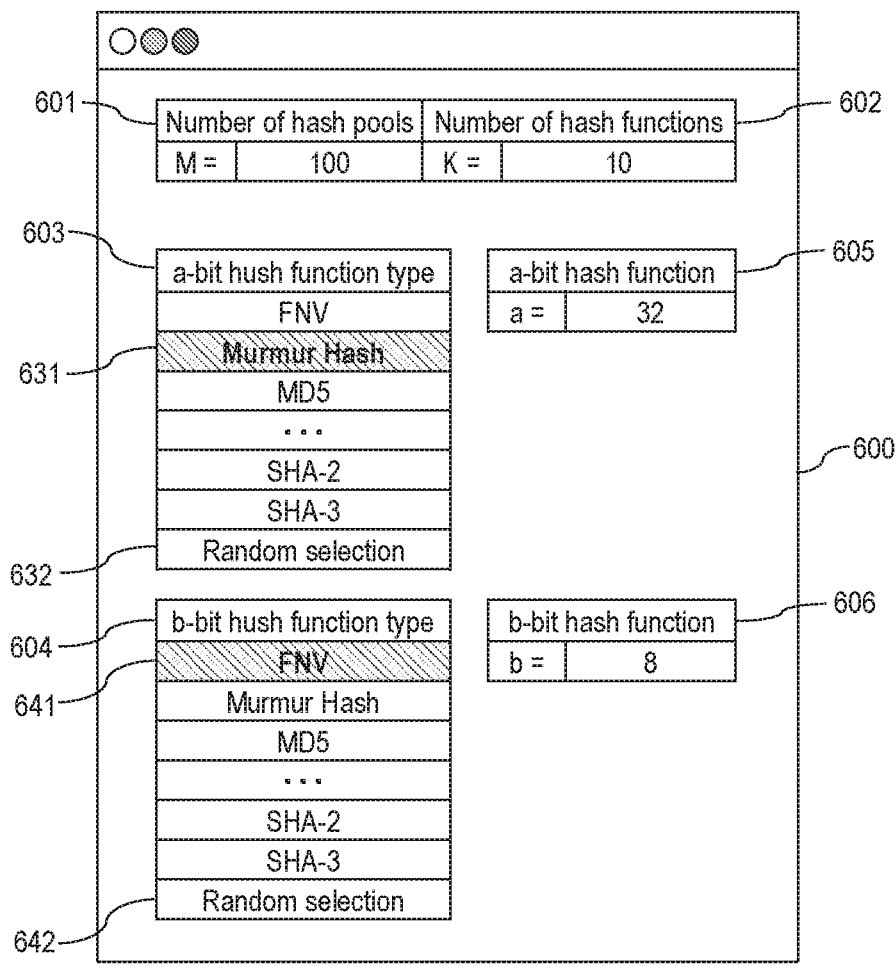
FIG. 6 is an explanatory diagram for illustrating a setting screen example in data analysis.

FIG. 6 is an explanatory diagram for illustrating a setting screen example in data analysis. The setting screen 600 is displayed on, for example, the monitor 305 of the client terminal 300 or the monitor 325 of the data analysis apparatus 320.

The setting screen 600 includes a hash pool count input field 601, a hash function count input field 602, an a-bit hash function type selection field 603, a b-bit hash function type selection field 604, a a-bit width input field 605, and a b-bit width input field 606.

The hash pool count input field 601 is a field for inputting the maximum number (total number) M of the number (hash pool count m) of hash pools $G^m$. The hash function count input field 602 is a field for inputting the maximum number (total number) K of the a-bit hash function count k.

The a-bit hash function type selection field 603 is a field for selecting a hash algorithm, which is a type of the a-bit hash function. Examples of the hash algorithm include FNV, MurmurHash, MD5, SHA-2, and SHA-3, and the hash algorithm can be selected through user's operation. In FIG. 6, MurmurHash 631 is selected. Further, a random selection 632 is an option for selecting at random any one of the hash algorithms of the a-bit hash function described above. When the random selection 632 is selected, in processing (FIG. 8) described later, every time the hash pool count m is incremented, any one of the hash algorithms of the a-bit hash function described above is selected at random.

The b-bit hash function type selection field 604 is a field for selecting a hash algorithm, which is a type of the b-bit hash function. Examples of the hash algorithm include FNV, MurmurHash, MD5, SHA-2, and SHA-3, and the hash algorithm can be selected through user's operation. In FIG. 6, FNV 641 is selected. Further, a random selection 642 is an option for selecting at random any one of the hash algorithms of the b-bit hash function described above. When the random selection 642 is selected, in the processing (FIG. 8) described later, every time the hash pool count m is incremented, any one of the hash algorithms of the b-bit hash function described above is selected at random.

The a-bit width input field 605 is a field for inputting a bit width a of the hash value of the a-bit hash function. The b-bit width input field 606 is a field for inputting a bit width b of the hash value of the b-bit hash function.

<Data Analysis Processing Procedure Example>

Figure 7:
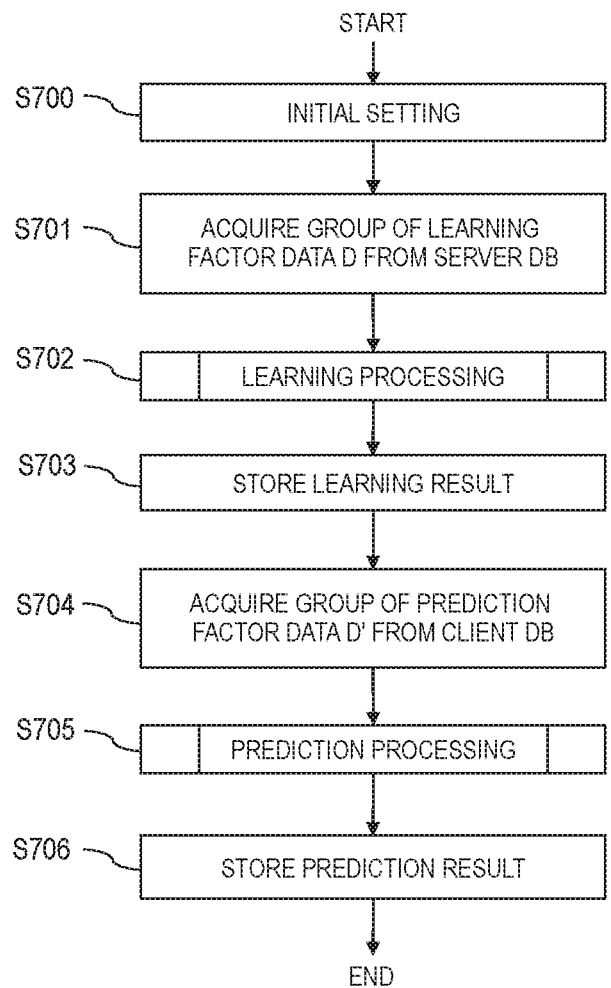
FIG. 7 is a flowchart for illustrating an example of a data analysis processing procedure to be executed by the data analysis system according to the first embodiment.

FIG. 7 is a flowchart for illustrating an example of a data analysis processing procedure to be executed by the data analysis system 3 according to the first embodiment. First, the learning processing module 361 executes an initial setting (Step S700). In the initial setting, values are input to or selected on the setting screen 600 of FIG. 6. In the initial setting, although not shown in FIG. 6, any one of data items of prediction values are selected for prediction from the data items 421 to 425. The sequence of values of the selected data items is referred to as "training data".

Next, the learning processing module 361 acquires a group of learning input data (group of learning factor data D) from the server DB 363 (Step S701). At this time, the learning processing module 361 generates the empty learning feature vector $X_n$ that does not contain elements as a feature vector. Then, the learning processing module 361 executes learning processing as illustrated in FIG. 1 and FIG. 2 (Step S702). Details of the learning processing (Step S702) are described with reference to FIG. 8. The learning result 365 is output by the learning processing (Step S702). Then, the learning processing module 361 stores the learning result 365 into the server DB 363 (Step S703).

Next, the prediction processing module 362 acquires the group of prediction input data (group of prediction factor data D') from the client DB 351, and acquires the learning result 365 from the server DB 363 (Step S704). Further, the prediction processing module 362 acquires the training data from the server DB 363. For example, when the prospect of remission 421 is selected as the data item i, the prediction processing module 362 acquires training data $y_n{}^i$, which is a sequence of values (partial remission (=3), stable disease (=2), progressive disease (=1), ..., remission (=4)) for 1 to N (=300,000) of the ID 400 for the prospect of remission 421 of the group of learning output data (group of learning diagnosis data Y). Further, the prediction processing module 362 generates the empty feature vector $X'_{n'}$ for prediction that does not contain elements as a feature vector.

Then, the prediction processing module 362 uses data acquired in Step S704 to execute prediction processing (Step S705). Details of the prediction processing (Step S705) are described with reference to FIG. 10. The prediction result 353 is output to the client terminal 300 by the prediction processing (Step S705).

The client terminal 300 stores the prediction result 353 into the client DB 351 (Step S706). The prediction result 353 is stored into a learning output DB of the prediction data set 352 stored in the client DB 351. For example, when the prospect of remission 421 is selected as any one of the data items i for prediction, the prediction result 353 is a prediction value $y'_{n'}{}^i$ of the prospect of remission 421 corresponding to each value n' of the ID 500 of the group of prediction factor data D'.

Figure 8:
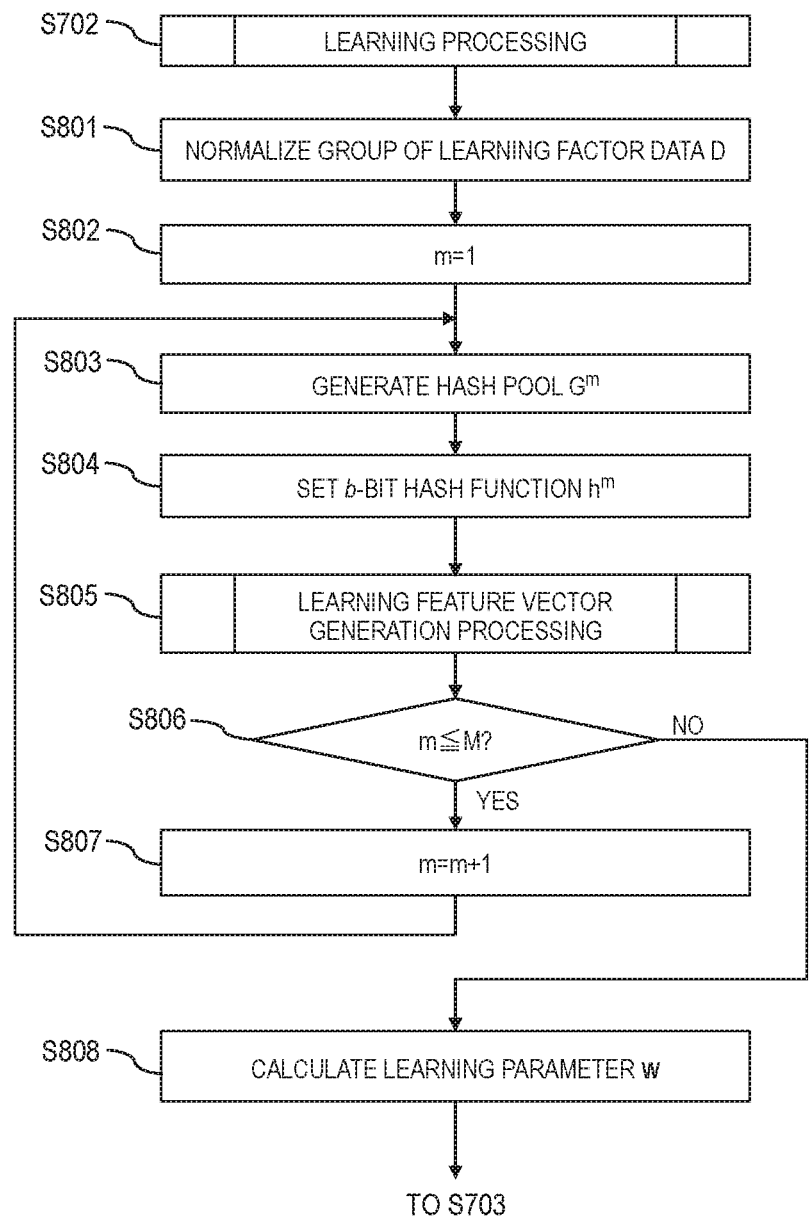
FIG. 8 is a flowchart for illustrating in detail an example of a processing procedure of the learning processing (Step S702) illustrated in FIG. 7.

FIG. 8 is a flowchart for illustrating in detail an example of a processing procedure of the learning processing (Step S702) illustrated in FIG. 7. First, as illustrated in (A) normalization of FIG. 2, the learning processing module 361 normalizes the group of learning input data (group of learning factor data D) (Step S801).

Specifically, for example, the learning processing module 361 normalizes the group of learning input data for each data item using Expression (5) given below for each learning factor data $D_n$. In Expression (5) given below, $x_n^i$ represents the value before normalization of the data item i having n as the ID 400, $x_{n\ max}^i$ represents the maximum value of a sequence of values $x_n^i$ of the data item i, $x_{n\ min}^i$ represents the minimum value of a sequence of values $x_n^i$ of the data item i, and $nor(x_n^i)$ represents a value obtained by normalizing $x_n^i$.

$$nor(x_n^i) = \frac{x_n^i - x_{n\ min}^i}{x_{n\ max}^i - x_{n\ min}^i} \quad (5)$$

Further, the learning factor data $nor(D_n)$ after normalization of the learning factor data $D_n$ is as follows.

$$nor(D_n) = \{nor(x_n^i) | i \in I\} \quad (6)$$

The maximum value $x_{n\ max}^i$ and the minimum value $x_{n\ min}^i$ are normalization coefficients, and the learning processing module 361 stores those values as normalization coefficients $Z_n^i$.

$$Z_n^i = \{(x_{n\ min}^i, x_{n\ max}^i) | i \in I\} \quad (7)$$

Next, the learning processing module 361 sets the hash pool count m to m=1 (Step S802), and generates the hash pool $G^m$ (Step S803). The learning processing module 361 generates a sub feature vector $x_n^m$, which is a $b^2$ dimensional zero vector for each learning factor data $nor(D_n)$ after normalization.

Next, the learning processing module 361 sets a b-bit hash function $h^m$ for the hash pool $G^m$ (Step S804). The b-bit hash function is a hash function that sets a random value as a seed. Specifically, for example, the learning processing module 361 uses an algorithm selected on the b-bit hash function type selection field 604 of the setting screen 600 of FIG. 6 to generate a hash table corresponding to the algorithm using a random value. This hash table is a table that associates the random value with a hash value obtained by substituting the random value in the b-bit hash function. The hash width of the hash value is a value that is input on the b-bit width input field 606 of FIG. 6.

Then, the learning processing module 361 executes learning feature vector generation processing as illustrated in FIG. 1 and FIG. 2 (Step S805). Details of the learning feature vector generation processing (Step S805) are described with reference to FIG. 9. In the learning feature vector generation processing (Step S805), the learning feature vector $X_n^m$ is generated for the hash pool $G^m$. The learning feature vector $X_n^m$ is a feature vector that indicates features of the learning factor data $D_n$ in the hash pool $G^m$.

After that, the learning processing module 361 determines whether or not the hash pool count m is equal to or smaller than the maximum value M of the hash pool count m (Step S806). When the hash pool count m is equal to or smaller than the maximum value M (Step S806: Yes), the learning processing module 361 needs to generate the hash pool $G^m$, and thus increments the hash pool count m (Step S807), and returns to Step S803.

On the contrary, when the hash pool count m is not equal to or smaller than the maximum value M (Step S806: No), the learning processing module 361 calculates the learning parameter w (Step S808). The learning feature vector $X_n^m$ generated in the learning feature vector generation processing (Step S805) is used for calculation of the learning parameter w (Step S808), and thus details thereof are described after description of the learning feature vector generation processing (Step S805).

In this manner, the learning processing module 361 ends the learning processing (Step S702) and executes Step S703.

Figure 9:
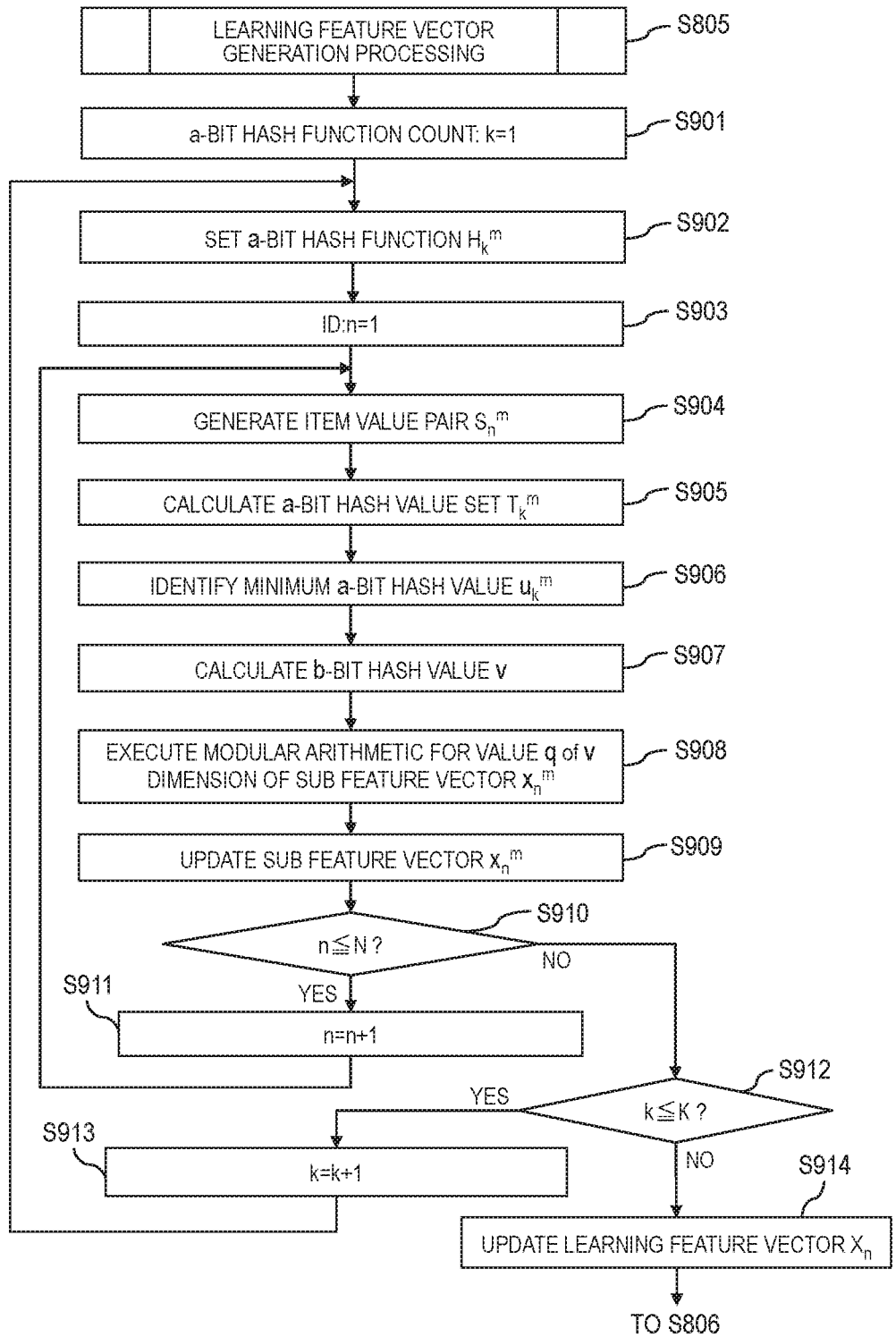
FIG. 9 is a flowchart for illustrating in detail an example of a processing procedure of the learning feature vector generation processing (Step S805) illustrated in FIG. 8.

FIG. 9 is a flowchart for illustrating in detail an example of a processing procedure of the learning feature vector generation processing (Step S805) illustrated in FIG. 8. First, the learning processing module 361 sets k=1 as an initial value of the a-bit hash function count k (Step S901).

Next, the learning processing module 361 sets an a-bit hash function $H_k^m$ for the hash pool $G^m$ (Step S902). The a-bit hash function is a hash function that sets a random value as a seed similarly to the b-bit hash function. Specifically, for example, the learning processing module 361 uses an algorithm selected on the a-bit hash function type selection field 603 of the setting screen 600 of FIG. 6 to generate a hash table corresponding to the algorithm using a random value. This hash table is a table that associates the random value with a hash value obtained by substituting the random value in the a-bit hash function. The hash width of the hash value is a value that is input on the a-bit width input field 605 of FIG. 6. This processing corresponds to (B) a-bit hash calculation of FIG. 2.

When the a-bit hash function $H_k^m$ that has the same m and k is generated in the hash pool $G^m$, the a-bit hash function $H_k^m$ is overwritten in the hash pool $G^m$.

Next, the learning processing module 361 sets the value n of the ID 400 to n=1 (Step S903), and generates an item value pair $S_n^m$ (Step S904). Specifically, for example, the learning processing module 361 selects $nor(x_n^i)$ whose value $x_n^i$ before normalization is not 0 for each $nor(x_n^i)$. The learning processing module 361 assigns j to the selected $nor(x_n^i)$ in place of i, and generates the item value pair $S_n^m$.

$$S_n^m = \{j, nor(x_n^j) | j \in J \subseteq I\ s.t.\ x_n^i \neq 0\} \quad (8)$$

Next, the learning processing module 361 calculates an a-bit hash value set $T_k^m$ (Step S905). Specifically, for example, the learning processing module 361 applies the a-bit hash function $H_k^m$ to the item value pair $S_n^m$, to thereby calculate the a-bit hash value set $T_k^m$. This processing corresponds to (C) weighting of FIG. 2.

$$T_k^m = \{t_j^m | j \in J\} \quad (9)$$

$$t_j^m = H_k^m(j) \times nor(x_n^j) \quad (10)$$

Then, the learning processing module 361 selects a minimum hash value $u_k^m$, which is the minimum value, from the a-bit hash value set $T_k^m$ calculated in Step S905 (Step S906). This processing corresponds to (D) minimum value selection of FIG. 2.

Next, the learning processing module 361 substitutes the minimum hash value $u_k^m$ in the b-bit hash function $h^m$ to calculate a b-bit hash value v (Step S907).

Then, the learning processing module 361 acquires the value q ($=q^{OLD}$) of a v dimension, which is obtained in Step S907, from the sub feature vector $x_n^m$, and executes modular arithmetic by odd-filtering in accordance with Expression (11) given below (Step S908).

$$q^{NEW} = mod(q^{OLD}+1, 2) \quad (11)$$

Then, the learning processing module 361 overwrites the value $q^{OLD}$ of the v dimension of the sub feature vector $x_n^m$ with the value $q^{NEW}$ calculated in Step 908 for storage (Step S909). Specifically, the base of Expression (11) is set to 2 so that the element of the v dimension repeats flip of from "0" to "1" or from "1" to "0". Further, the base is set to 2, and the value of the v dimension is aggregated into "0" or "1", and thus it is possible to achieve memory saving. This processing corresponds to (B) of FIG. 1.

After that, the learning processing module 361 determines whether or not the value n of the ID 400 is equal to or smaller than the maximum value N (Step S910). When the value n of the ID 400 is equal to or smaller than the maximum value N (Step S910: Yes), there is an unselected ID to be processed, and thus the learning processing module 361 increments n (Step S911), and returns to Step S904.

On the contrary, when n is not equal to or smaller than the maximum value N (Step S910: No), the learning processing module 361 determines whether or not the a-bit hash function count k is equal to or smaller than the maximum value K (Step S912). When the a-bit hash function count k is equal to or smaller than the maximum value K (Step S912: Yes), there is an a-bit hash function $H_k^m$ to be tried, and thus the learning processing module 361 increments the a-bit hash function count k (Step S913), and returns to Step S902.

On the contrary, when k is not equal to or smaller than the maximum value K (Step S912: No), the learning processing module 361 uses Expression (12) given below to stack the sub feature vector $x_n^m$ on the feature vector $X_n$, to thereby update the feature vector $X_n$ (Step S914).

$$X_n = \text{stack}(X_n, x_n^m) \quad (12)$$

When a vector $c=(c1, c2)^t$ and a vector $d=(d1, d2)^t$ are set, the stack function of Expression (12) is a function that concatenates the vectors c and d as shown in Expression (13) given below.

$$\text{stack}(c,d) = (c1, c2, d1, d2)^t \quad (13)$$

With this, the learning feature vector $X_n$ is generated for the value n of the ID 400, and the learning processing module 361 ends the learning feature vector generation processing (Step S805) to execute Step S806.

Then, referring back to FIG. 8, in Step S808, the learning parameter w is calculated. Specifically, when $y_n^i$ is set as training data, the learning parameter w is calculated in accordance with Expression (14) given below.

$$y_n^i = f(X_n, w) \quad (14)$$

For example, when the prospect of remission 421 is selected from the group of learning output data (group of learning diagnosis data Y) for the data item i to be learned, the training data $y_n^i$ is a sequence of values (partial remission (=3), stable disease (=2), progressive disease (=1), . . . , remission (=4)) for 1 to N (=300,000) of the ID 400.

For example, a discriminant function is used as the function f of Expression (14). Examples of the discriminant function include known functions using SVM and a neural network. When quantity data, for example, the prescription amount of a drug, is selected as training data, a regression function is used as the function f. For example, a known SVM regression function is used.

As a result, the learning processing module 361 stores the normalization coefficient $Z_n^i$, the learning parameter w, and the hash pool family G shown in Expression (7) into the server DB 363 as the learning result 365. The hash pool family G contains the generated a-bit hash function $H_k^m$ and the b-bit hash function $h^m$.

Figure 10:
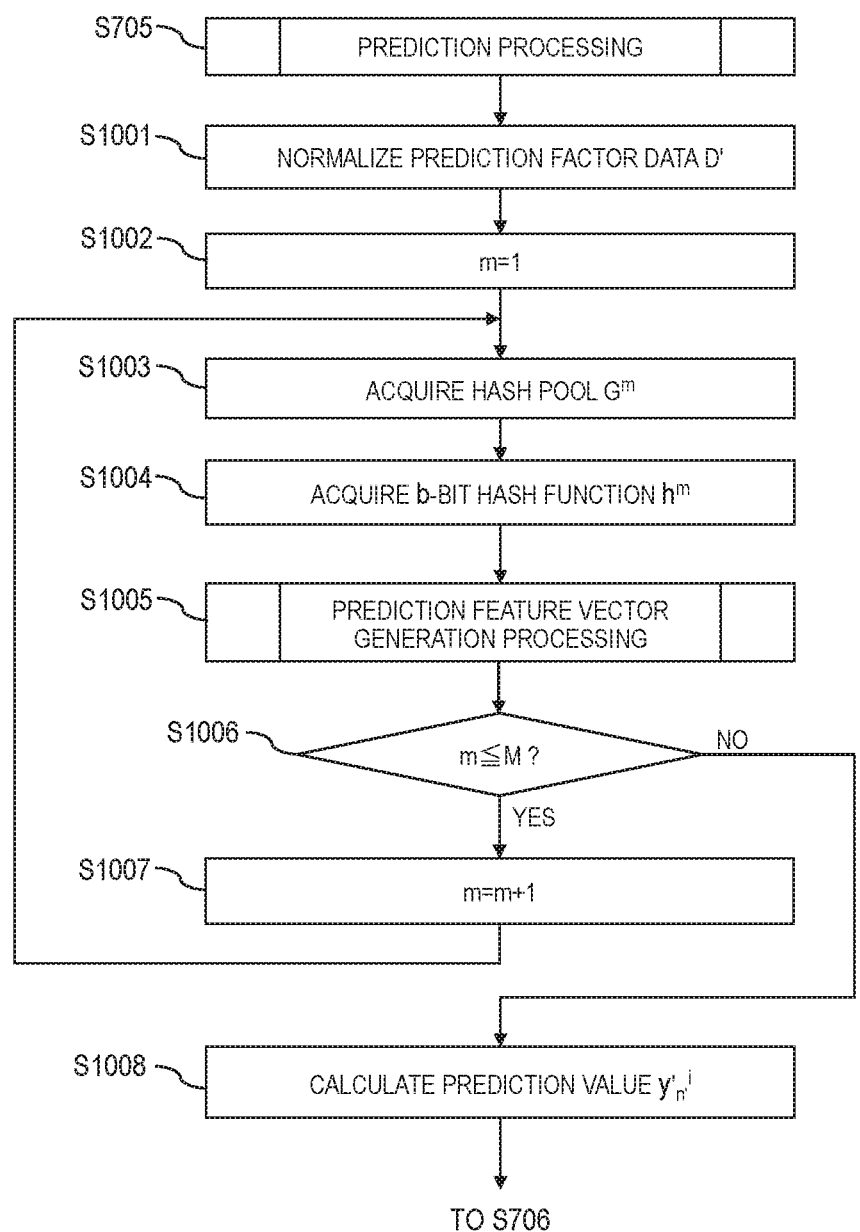
FIG. 10 is a flowchart for illustrating in detail an example of a processing procedure of the prediction processing (Step S705) illustrated in FIG. 7.

FIG. 10 is a flowchart for illustrating in detail an example of a processing procedure of the prediction processing (Step S705) illustrated in FIG. 7. First, the prediction processing module 362 normalizes the group of prediction input data (group of prediction factor data D') with the same technique as that of Step S801 (Step S1001). Specifically, for example, the prediction processing module 362 normalizes each prediction factor data $D'_{n'}$ for each data item in accordance with Expression (15) given below. In Expression (15), $x'_{n'}^i$ represents the value of the data item i whose ID 500 before normalization is n, $x'_{n'max}^i$ represents the maximum value of the sequence of values $x'_{n'}^i$ of the data item i, $x'_{n'min}^i$ represents the minimum value of the sequence of values $x'_{n'}^i$ of the data item i, and $nor(x'_{n'}^i)$ represents a value obtained by normalizing $x'_{n'}^i$.

$$nor(x_{n'}^{i}) = \frac{x_{n'}^{i} - x_{n'min}^{i}}{x_{n'max}^{i} - x_{n'min}^{i}} \quad (15)$$

Further, the prediction factor data $nor(D'_{n'})$ after normalization of the prediction factor data $D'_{n'}$ is as follows.

$$nor(D'_{n'}) = \{nor(x'_{n'}^i) | i \in I'\} \quad (16)$$

The maximum value $x'_{n'max}^i$ and the minimum value $x_{n'min}^i$ are normalization coefficients, and the prediction processing module 362 stores those coefficients as a normalization set $Z'_{n'}^i$.

$$Z'_{n'}^i = \{(x'_{n'min}^i, x'_{n'max}^i) | i \in I'\} \quad (17)$$

Next, the prediction processing module 362 sets the hash pool count m to m=1 (Step S1002), and acquires the hash pool $G^m$ from the hash pool family G contained in the learning result 365 (Step S1003). The prediction processing module 362 generates a sub feature vector $x'_{n'}^m$, which is a $b^2$ dimensional zero vector, for each prediction factor data $nor(D'_{n'})$ after normalization.

Next, the prediction processing module 362 acquires the b-bit hash function $h^m$ from the hash pool family G contained in the learning result 365 for the hash pool $G^m$ (Step S1004).

Then, the prediction processing module 362 executes prediction feature vector generation processing as illustrated in FIG. 1 and FIG. 2 (Step S1005). Details of the prediction feature vector generation processing (Step S1005) are described with reference to FIG. 11. In the prediction feature vector generation processing (Step S1005), a prediction feature vector $x'_{n'}^m$ is generated for the hash pool $G^m$. The prediction feature vector $x'_{n'}^m$ is a feature vector that indicates features of the prediction factor data $D'_{n'}$ in the hash pool $G^m$.

After that, the prediction processing module 362 determines whether or not the hash pool count m is equal to or smaller than the maximum value M of the hash pool count m (Step S1006). When the hash pool count m is equal to or smaller than the maximum value M (Step S1006: Yes), the prediction processing module 362 needs to acquire the hash pool $G^m$, and thus increments the hash pool count m (Step S1007), and returns to Step S1003.

On the contrary, when the hash pool count m is not equal to or smaller than the maximum value M (Step S1006: No), the prediction processing module 362 calculates a prediction value $y'_{n'}^i$ (Step S1008). For example, when the prospect of remission 421 is selected as any one of the data items i for prediction, the prediction processing module 362 calculates the prediction value $y'_{n'}^i$ of the prospect of remission 421 corresponding to each value n' of the ID 500 of the group of prediction factor data D'. The prediction feature vector $x'^m_{n'}$ generated in the prediction feature vector generation processing (Step S1005) is used for calculation of the prediction value $y'^i_{n'}$ (Step S1008), and thus details thereof are described after description of the prediction feature vector generation processing (Step S1005).

In this manner, the prediction processing module 362 ends the prediction processing (Step S705) and executes Step S706.

Figure 11:
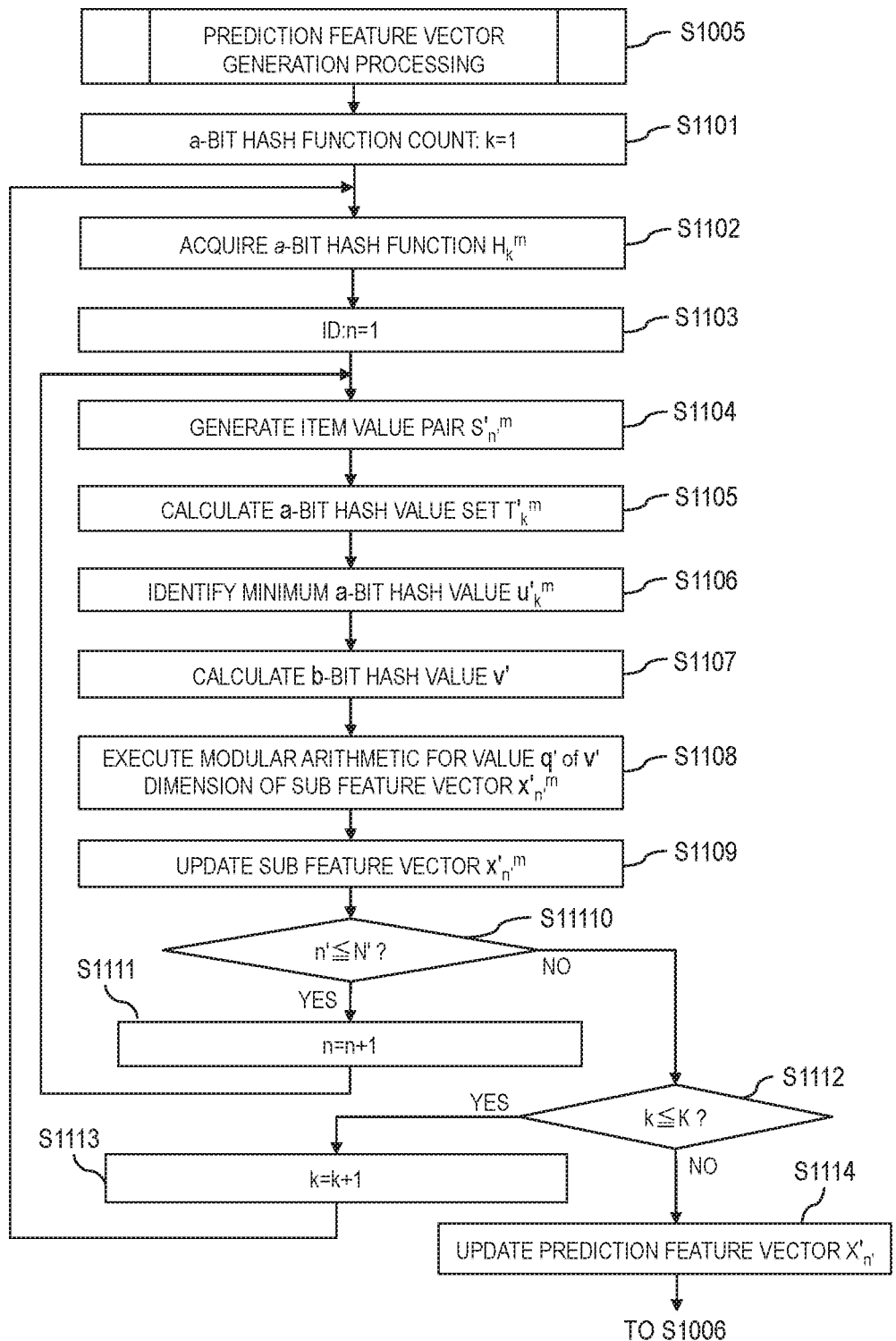
FIG. 11 is a flowchart for illustrating in detail an example of a processing procedure of the prediction feature vector generation processing (Step S1005) illustrated in FIG. 10.

FIG. 11 is a flowchart for illustrating in detail an example of a processing procedure of the prediction feature vector generation processing (Step S1005) illustrated in FIG. 10. First, the prediction processing module 362 sets k=1 as the initial value of the a-bit hash function count k (Step S1101).

Next, the prediction processing module 362 acquires the a-bit hash function $H^m_k$ of the hash pool $G^m$ from the hash pool family G contained in the learning result 365 (Step S1102).

Next, the prediction processing module 362 sets the value n' of the ID 500 to n'=1 (Step S1103), and generates an item value pair $S'^m_{n'}$ (Step S1104). Specifically, for example, the prediction processing module 362 selects $\text{nor}(x'^i_{n'})$ whose value $x'^i_{n'}$ before normalization is not 0 for each $\text{nor}(x'^i_{n'})$. The prediction processing module 362 assigns j to the selected $\text{nor}(x'^i_{n'})$ in place of i, and generates the item value pair $S'^m_{n'}$.

$$S'^m_{n'} = \{j, \text{nor}(x'^i_{n'}) | j \in J' \subseteq I \text{ s.t. } x'^i_{n'} \neq 0\} \quad (18)$$

Next, the prediction processing module 362 calculates the a-bit hash value set $T'^m_k$ (Step S1105). Specifically, for example, the prediction processing module 362 applies the a-bit hash function $H^m_k$ to the item value pair $S'^m_{n'}$, to thereby calculate the a-bit hash value set $T'^m_k$. This processing corresponds to (C) weighting of FIG. 2.

$$T'^m_k = \{t'^m_j | j \in J'\} \quad (19)$$

$$t'^m_j = H^m_k(j) \times \text{nor}(x'^i_{n'}) \quad (20)$$

Then, the prediction processing module 362 selects a minimum hash value $u'^m_k$, which is the minimum value, from the a-bit hash value set $T'^m_k$ calculated in Step S1105 (Step S1106). This processing corresponds to (D) minimum value selection of FIG. 2.

Next, the prediction processing module 362 substitutes the minimum hash value $u'^m_k$ in the b-bit hash function $h^m$ to calculate a b-bit hash value v' (Step S1107).

Then, the prediction processing module 362 acquires the value q' (=$q'^{OLD}$) of the v' dimension, which is obtained in Step S1107, from the sub feature vector $x'^m_{n'}$, and executes odd-filtering calculation in accordance with Expression (21) given below (Step S1108).

$$q'^{NEW} = \text{mod}(q'^{OLD}+1, 2) \quad (21)$$

Then, the prediction processing module 362 overwrites the value $q'^{OLD}$ of the v' dimension of the sub feature vector $x'^m_{n'}$ with the value $q'^{NEW}$ calculated in Step 1108 for storage (Step S1109). Specifically, the base of Expression (21) is set to 2 so that the element of the v' dimension repeats flip of from "0" to "1" or from "1" to "0". Further, the base is set to 2, and the value of the v' dimension is aggregated into "0" or "1", and thus it is possible to achieve memory saving. This processing corresponds to (B) of FIG. 1.

After that, the prediction processing module 362 determines whether or not the value n' of the ID 500 is equal to or smaller than the maximum value N' (Step S1110). When the value n' of the ID 500 is equal to or smaller than the maximum value N' (Step S1110: Yes), there is an unselected ID to be processed, and thus the prediction processing module 362 increments n' (Step S1111), and returns to Step S1104.

On the contrary, when n' is not equal to or smaller than the maximum value N (Step S1110: No), the prediction processing module 362 determines whether or not the a-bit hash function count k is equal to or smaller than the maximum value K (Step S1112). When the a-bit hash function count k is equal to or smaller than the maximum value K (Step S1112: Yes), there is an a-bit hash function $H^m_k$ to be tried, and thus the prediction processing module 362 increments the a-bit hash function count k (Step S1113), and returns to Step S1102.

On the contrary, when k is not equal to or smaller than the maximum value K (Step S1112: No), the prediction processing module 362 uses the stack function described in Expressions (12) and (13) to stack the sub feature vector $x'^m_{n'}$ on the prediction feature vector to thereby update the prediction feature vector $X'_{n'}$ (Step S1114).

$$X'_{n'} = \text{stack}(X'_{n'}, x'^m_{n'}) \quad (22)$$

With this, the learning feature vector $X'_{n'}$ is generated for the value n' of the ID 500, and the prediction processing module 362 ends the prediction feature vector generation processing (Step S1005) to execute Step S1006.

Then, referring back to FIG. 10, in Step S1008, the prediction value $y'^i_{b'}$ is calculated. Specifically, the prediction value $y'^i_{n'}$ is calculated in accordance with Expression (23) given below using the function f shown in Expression (14), the learning parameter w, and the prediction feature vector $X'_{n'}$.

$$y'^i_{n'} = f(X'_{n'}, w) \quad (23)$$

For example, when the prospect of remission 421 is selected from the group of prediction output data (group of prediction diagnosis data Y') as the data item i, the prediction value $y'^i_{n'}$ is a sequence of prediction values for 1 to N (=300,000) of the ID 500.

In this manner, according to the first embodiment, even when there are an enormous amount of data N and N' and an enormous number of data items I and I', it is possible to achieve rapid and accurate data analysis while achieving memory saving. Further, even when the values of the data items I and I' take multiple values and real values, it is possible to achieve rapid and accurate data analysis while achieving memory saving.

Second Embodiment

In a second embodiment of this invention, in the aggregation processing illustrated in part (B) of FIG. 1 of the first embodiment, there is given an example of executing folding calculation in place of modular calculation by odd-filtering. The folding calculation is processing of adding the value $x^i_n$ of the data item i to the value of the feature vector in an accumulated manner, and this processing enables the data analysis system 3 to directly analyze the data item i of multiple values and real values. In other words, compared to the first embodiment, the second embodiment relates to a configuration example of putting a more priority on the accuracy of data analysis than the memory consumption amount of a computer. In the description of the second embodiment, the difference from the first embodiment is mainly described, and description of the same processing as that of the first embodiment is omitted here.

Figure 12:
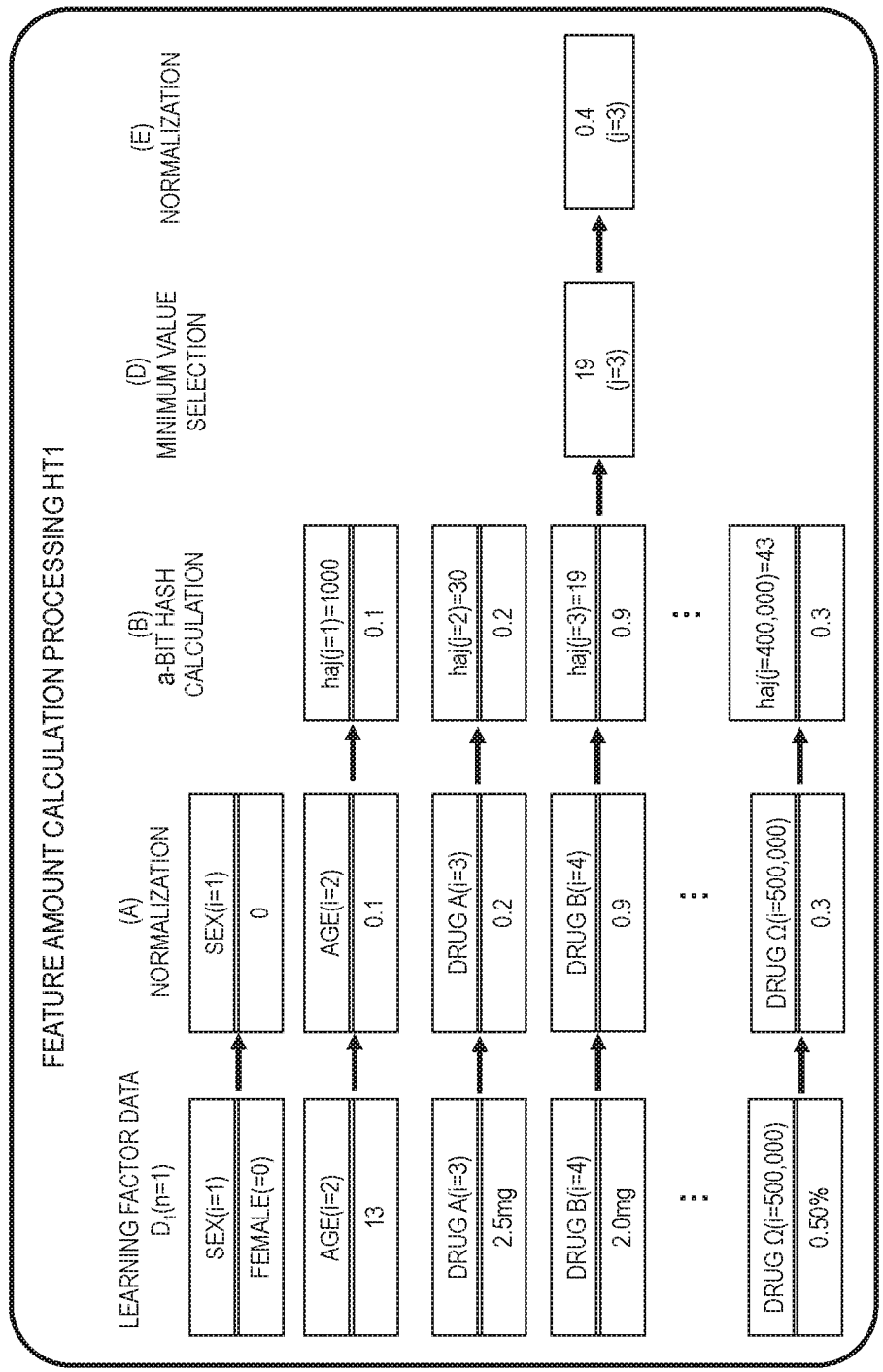
FIG. 12 is an explanatory diagram for illustrating in detail an example of processing of the feature amount calculation processing HT1 according to the second embodiment.

FIG. 12 is an explanatory diagram for illustrating in detail an example of processing of the feature amount calculation processing HT1 according to the second embodiment. In the feature amount calculation processing HT1 according to the first embodiment illustrated in FIG. 2, (C) weighting is executed after (B) a-bit hash calculation, but in the second embodiment, (D) minimum value selection is executed without executing (C) weighting. After that, the feature amount calculation processing HT1 executes (E) normalization of the minimum value selected in (D) minimum value selection. (E) normalization is executed with the same calculation method as that of (A) normalization.

In the feature amount calculation processing HT1 of FIG. 12, the description is given using the learning factor data $D_1$, but the feature amount calculation processing HT1 is executed similarly for the learning factor data $D_2$ to $D_N$. Further, in FIG. 12, the description is given using the feature amount calculation processing HT1, but the same processing is executed similarly for other feature amount calculation processing HT2 to HTK.

Figure 13:
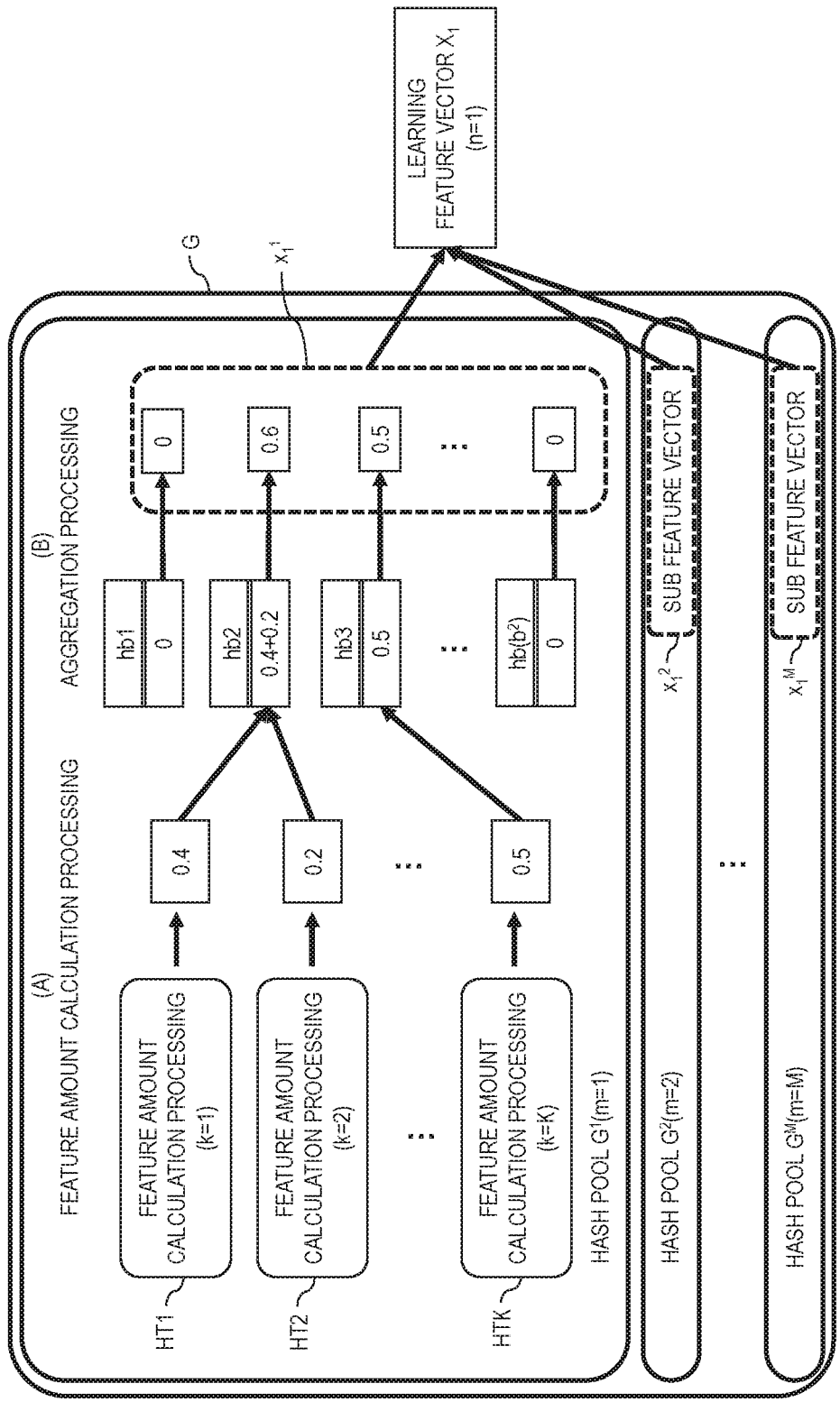
FIG. 13 is an explanatory diagram for illustrating an example of generation of a feature vector according to the second embodiment.

FIG. 13 is an explanatory diagram for illustrating an example of generation of a feature vector according to the second embodiment. In the example of generation of the feature vector according to the first embodiment illustrated in FIG. 1, modular calculation is executed by odd-filtering in (B) aggregation, but instead, folding calculation is executed in (B) aggregation of the second embodiment.

In the folding calculation, a hash value corresponding to the normalized minimum value, which is the output from the feature amount calculation processing HTk, is obtained by the b-bit hash function $h^m$. In the folding calculation, a normalized minimum value having the same hash value is added in an accumulated manner.

For example, the normalized minimum value "0.4", which is obtained in the feature amount calculation processing HT1 using the learning factor data $D_1$, corresponds to the hash value hb2 among the hash values hb1 to hb($b^2$) of the hash table generated by the b-bit hash function. Therefore, the aggregated value corresponding to the hash value hb2 results in "0.4" through addition of the normalized minimum value "0.4" to the initial value of "0" in an accumulated manner. Next, the normalized minimum value "0.2", which is obtained in the feature amount calculation processing HT2 using the learning factor data $D_1$, also corresponds to the hash value hb2. Thus, the normalized minimum value "0.2" is added to "0.4" to obtain "0.6" as the aggregation value corresponding to the hash value hb2.

As the value of b becomes smaller, the same hash value is more likely to be hit. In (B) aggregation processing, this property is used to aggregate minimum values obtained in (A) feature amount calculation processing.

In this manner, through completion of (B) aggregation processing, the sub feature vector $x_1^1$ that arranges the aggregated values of from the hash values hb1 to hb($b^2$) is generated. The sub feature vectors $x_1^2$ to $x_1^M$ are generated similarly for the hash pools $G^2$ to $G^m$. Then, through concatenation of the sub feature vectors $x_1^1$ to $x_1^M$, the feature vector $X_1$, which indicates features of the learning factor data $D_1$, is generated. The feature vectors $X_2$ to $X_N$, which indicate features of the learning factor data $D_2$ to $D_N$, are generated similarly for the learning factor data $D_2$ to $D_N$.

<Learning Feature Vector Generation Processing (Step S805)>

Figure 14:
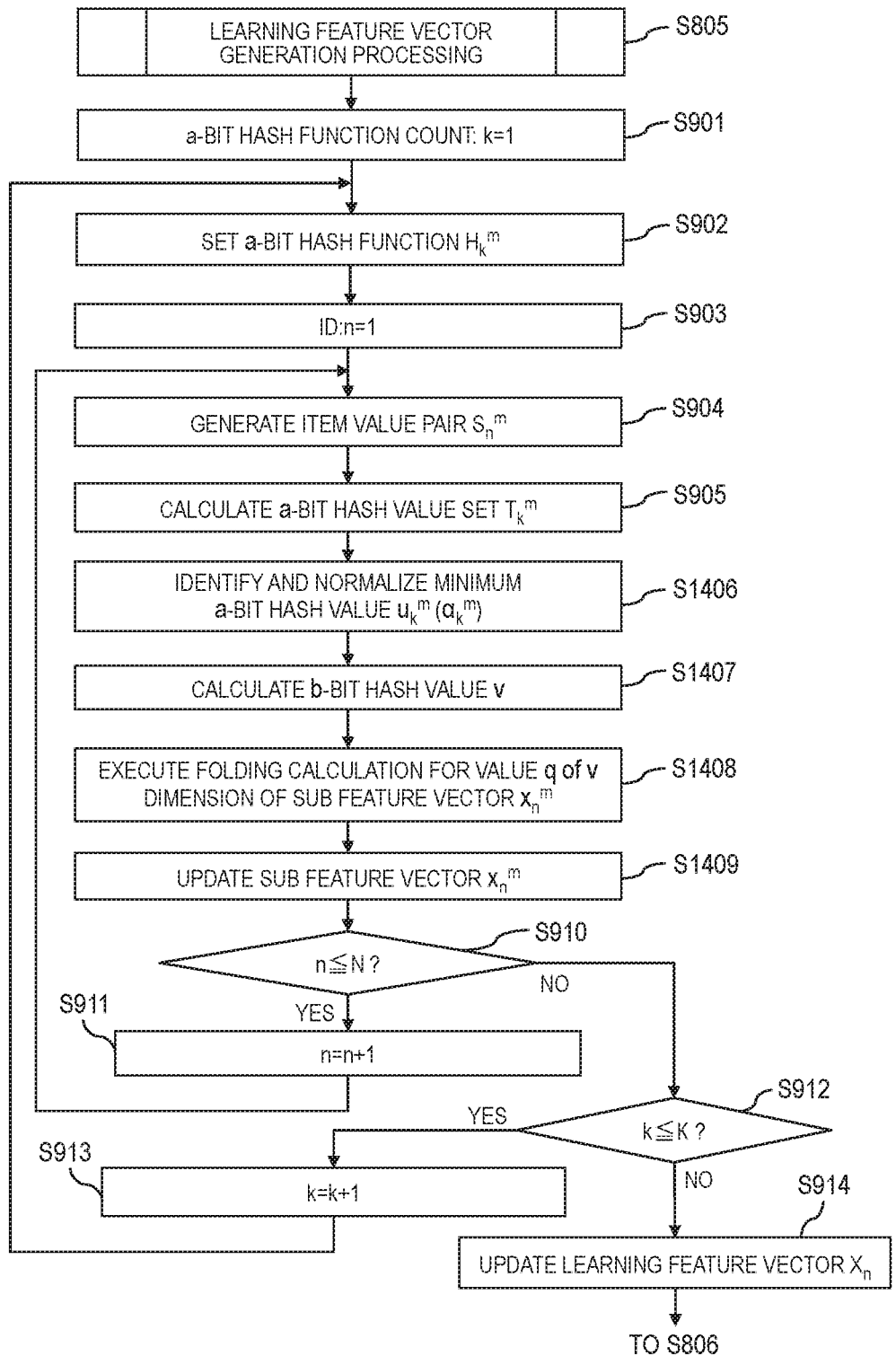
FIG. 14 is a flowchart for illustrating in detail an example of a processing procedure of the learning feature vector generation processing (Step S805) according to the second embodiment.

FIG. 14 is a flowchart for illustrating in detail an example of a processing procedure of the learning feature vector generation processing (Step S805) according to the second embodiment. The same step as that of the learning feature vector generation processing (Step S805) according to the first embodiment illustrated in FIG. 9 is denoted by the same step number, and a description thereof is omitted here.

After Step S905, the learning processing module 361 identifies the minimum value $u_k^m$ from among the group of a-bit hash values obtained by the a-bit hash function $H_k^m$ as illustrated in (B) minimum value selection of FIG. 12, and normalizes the minimum value $u_k^m$ as illustrated in (E) normalization, to thereby calculate a normalized minimum value $\alpha_k^m$ (Step S1406).

After that, the learning processing module 361 substitutes the normalized minimum value $\alpha_k^m$ in the b-bit hash function $h^m$ to calculate the b-bit hash value v (Step S1407).

Then, the learning processing module 361 acquires the value q (=$q^{OLD}$) of the v dimension, which is obtained in Step S1407, from the sub feature vector $x_n^m$, and executes folding calculation in accordance with Expression (24) given below (Step S1408).

$$q^{NEW} = q^{OLD} + \alpha_k^m \quad (24)$$

Then, the learning processing module 361 overwrites the value $q^{OLD}$ of the v dimension of the sub feature vector $x_n^m$ with the value $q^{NEW}$ calculated in Step S1408 for storage (Step S1409). In this manner, through addition of the normalized minimum value $\alpha_k^m$ having the same b-bit hash value, the features of the learning factor data $D_n$ can be reflected more in detail. Therefore, it is possible to achieve more accurate data analysis. This processing corresponds to (B) of FIG. 13.

In this manner, in the second embodiment, the a-bit hash function is used to calculate the normalized minimum value of the feature amount corresponding to the value of each data item of the learning factor data $D_n$ by the feature amount calculation processing HTk, and the b-bit hash function is used to aggregate the normalized minimum values. Therefore, it is possible to achieve more rapid data analysis.

Further, the normalized minimum values of the learning factor data $D_n$ are aggregated by folding calculation to generate the learning feature vector $X_n$, and thus each element of the learning feature vector $X_n$ is a value that takes two values, multiple values, and real values of respective data items of the learning factor data $D_n$ into consideration. Therefore, it is possible to achieve more accurate data analysis.

Further, in the aggregation processing, the normalized minimum values are aggregated by folding calculation, to thereby be able to represent features of the learning factor data $D_n$ more in detail. Therefore, the second embodiment is appropriate for a case in which the value of a data item takes multiple values or real values, and thus it is possible to achieve more accurate data analysis.

Third Embodiment

A third embodiment of this invention is an example of achieving a more accurate sub feature vector generated in the first embodiment and the second embodiment. Specifically, the data analysis system 3 according to the third embodiment identifies a sub feature vector that exhibits a low analysis accuracy before obtaining the learning parameter w in the learning processing (Step S702), and re-executes the learning feature vector generation processing (Step S805) without stacking the sub feature vector with a stack function until the analysis accuracy reaches a predetermined level or more.

With this, a learning feature vector having a sub feature vector whose analysis accuracy exhibits a predetermined level or more is generated, and thus a more accurate learning parameter w can be calculated. Through use of such an accurate learning parameter w in the prediction processing (Step S704), it is possible to achieve improvement of the accuracy of the prediction value.

Cross-validation is executed, for example, as a system of re-executing the learning feature vector generation processing (Step S805).

Figure 15:
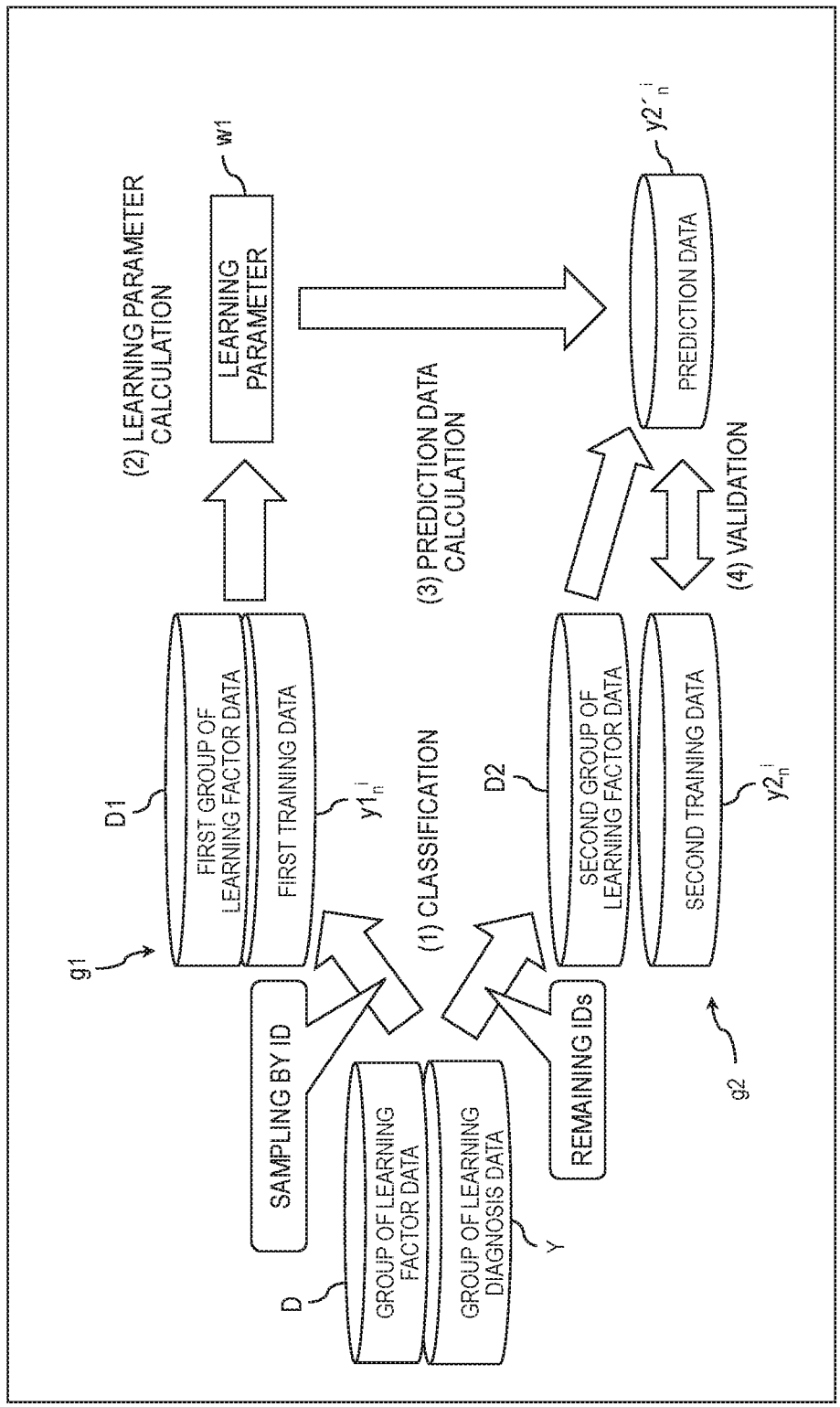
FIG. 15 is an explanatory diagram for illustrating an example of execution of the cross-validation.

FIG. 15 is an explanatory diagram for illustrating an example of execution of the cross-validation. In the cross-validation, the learning processing module 361 executes (1) classification, (2) learning parameter calculation, (3) prediction data calculation, and (4) validation in the stated order.

In (1) classification, the learning processing module 361 classifies the group of learning factor data D and the group of learning diagnosis data Y into two groups by sampling arbitrary IDs 400 for some data item i. A first group g1, which is obtained by sampling arbitrary IDs, contains a first group of learning factor data D1 and first training data $y1_n^i$. A second group g2, which is a group of remaining IDs 400, contains a second group of learning factor data D2 and second training data $y2_n^i$.

In (2) learning parameter calculation, the learning processing module 361 assigns the first group of learning factor data D1 and the first training data $y1_n^i$ to a classifier, for example, SVM, to calculate the learning parameter w1. The processing illustrated in Step S808 of FIG. 8 described above may be applied to calculate the learning parameter w1.

In (3) prediction data calculation, the learning processing module 361 uses the learning parameter w1 and the second group of learning factor data D2 by processing similar to that described in Step S1008 of FIG. 10 to calculate the prediction data $y2'_n^i$.

In (4) validation, the learning processing module 361 compares the second training data $y2_n^i$ with the prediction data $y2'_n^i$ to calculate the difference for each n as an error. Then, the learning processing module 361 calculates the square root of sum of squares of errors for respective n, and calculates the reciprocal of the square root as a prediction accuracy.

The learning processing module 361 changes IDs to be sampled in (1), to execute the processing of from (1) to (4) a plurality of times. Then, the learning processing module 361 calculates an average prediction accuracy, which is an average value of prediction accuracies obtained in (4) validation of respective times. Statistical values satisfying other statistical conditions, such as the maximum value, the minimum value, the median value, and a randomly selected value of the prediction accuracies, may be calculated instead of the average of prediction accuracies. In the following description, a description is given using the average prediction accuracy as an example.

The learning parameter w1 and the prediction data $y2'_n^i$ calculated in (2) learning parameter calculation do not satisfy the required accuracy until the average prediction accuracy exceeds a threshold value. In this case, the learning processing module re-generates the b-bit hash function $h^m$ and the a-bit hash function $H_k^m$, to re-execute cross-validation.

Figure 16:
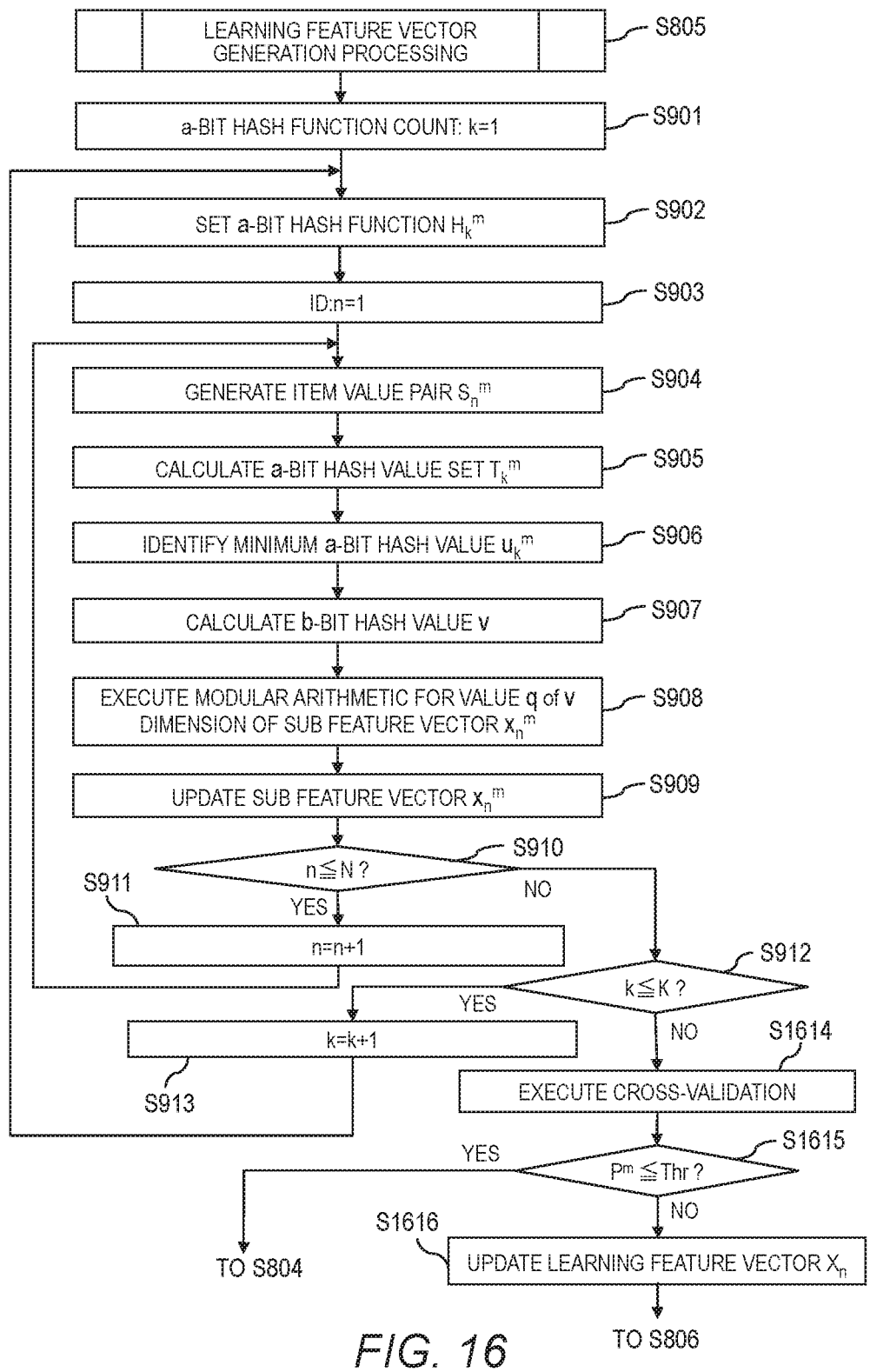
FIG. 16 is a flowchart for illustrating in detail a processing procedure example 1 of the learning feature vector generation processing (Step S805) according to the third embodiment.

FIG. 16 is a flowchart for illustrating in detail a processing procedure example 1 of the learning feature vector generation processing (Step S805) according to the third embodiment. FIG. 16 is an example of a processing procedure of executing cross-validation in the learning feature vector generation processing (Step S805) according to the first embodiment illustrated in FIG. 9. In FIG. 16, the same step as that of FIG. 9 is denoted by the same step number, and a description thereof is omitted here.

Figure 17:
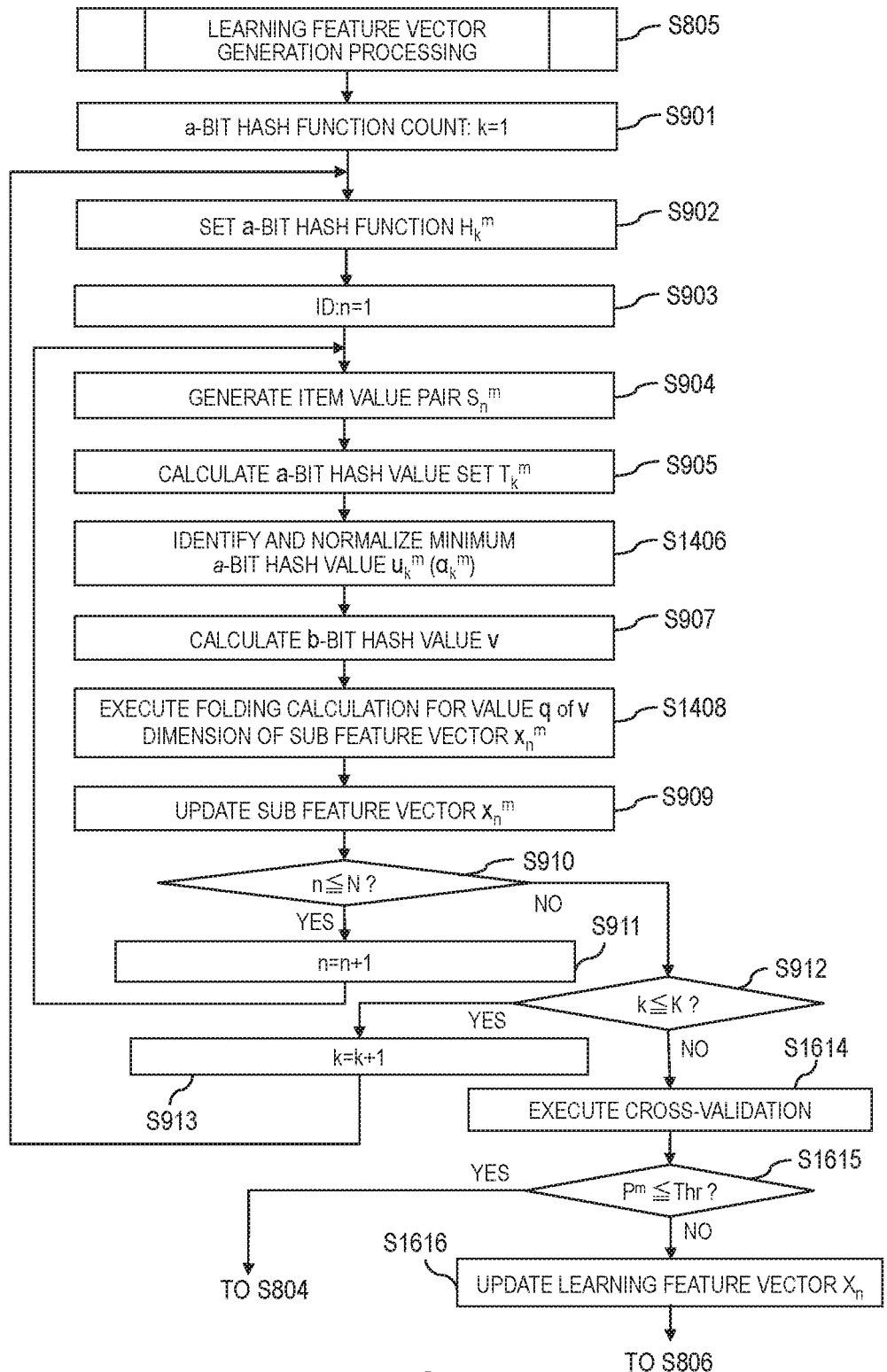
FIG. 17 is a flowchart for illustrating in detail a processing procedure example 2 of the learning feature vector generation processing (Step S805) according to the third embodiment.

FIG. 17 is a flowchart for illustrating in detail a processing procedure example 2 of the learning feature vector generation processing (Step S805) according to the third embodiment. FIG. 17 is an example of a processing procedure of executing cross-validation in the learning feature vector generation processing (Step S805) according to the second embodiment illustrated in FIG. 14. In FIG. 17, the same step as that of FIG. 14 is denoted by the same step number, and a description thereof is omitted here.

In FIG. 16 and FIG. 17, after Step S912, the learning processing module 361 executes cross-validation illustrated in FIG. 15 (Step S1614). In the hash pool $G^m$, the average prediction accuracy obtained in cross-validation is set as $P^m$, and a threshold is set as Thr. When $P^m \leq$ Thr (Step S1615: Yes), the learning processing module 361 proceeds to Step S804 of FIG. 8, re-generates the b-bit hash function (Step S804), and uses the re-generated b-bit hash function to re-execute the learning feature vector generation processing (Step S805) of FIG. 16 (in the case of first embodiment) and FIG. 17 (in the case of second embodiment).

In this manner, according to the learning feature vector generation processing (Step S805) of FIG. 16, cross-validation is applied in the first embodiment. Therefore, in the first embodiment, it is possible to obtain a reliable learning parameter w and achieve improvement of the data analysis accuracy.

Further, according to the learning feature vector generation processing (Step S805) of FIG. 17, cross-validation is applied in the second embodiment. Therefore, in the second embodiment, it is possible to obtain a reliable learning parameter w and achieve improvement of the data analysis accuracy.

As described above, according to the third embodiment, a hash value is generated by the a-bit hash function, which is weighted by the value of a data item, and a b-bit hash value is calculated from the generated hash value by the b-bit hash function, to thereby implement dimension reduction of a feature vector. With this, it is possible to achieve rapid and accurate data analysis. Further, even when the number of data items is enormous and those data items take multiple values and real values, it is possible to achieve rapid and accurate data analysis while achieving memory saving.

In the embodiments described above, the description is given using the drug efficacy analysis as an example, but this invention can be applied to product recommendation. In this case, the ID 400 of the learning input DB 410 illustrated in FIG. 4 represents a customer instead of a patient, the data items 411 to 415 represent products or services (or may be categories of products or services), and the values represent the number of purchases or the purchase amount (in the case of products) or the number of uses or the use charge (in the case of services). Further, the data items 421 to 425 of the learning output DB 420 represent types of tastes that represent, for example, a purchase tendency of a customer and interest of the customer. The same applies to the prediction input DB 510 and the learning output DB 520.

Further, in the case of analysis of a news article, the ID 400 of the learning input DB 410 illustrated in FIG. 4 represents a news article posted on a newspaper, a magazine, or a web page, and the data items 411 to 415 represent words and values thereof represent a frequency of appearance of those words. Further, the data items 421 to 425 of the learning output DB 420 represent categories of a news article, such as politics, society, sports, and weather. The same applies to the prediction input DB 510 and the learning output DB 520.

It should be noted that this invention is not limited to the above-mentioned embodiments, and encompasses various modification examples and the equivalent configurations within the scope of the appended claims without departing from the gist of this invention. For example, the above-mentioned embodiments are described in detail for a better understanding of this invention, and this invention is not necessarily limited to what includes all the configurations that have been described. Further, a part of the configurations according to a given embodiment may be replaced by the configurations according to another embodiment. Further, the configurations according to another embodiment may be added to the configurations according to a given embodiment. Further, a part of the configurations according to each embodiment may be added to, deleted from, or replaced by another configuration.

Further, a part or entirety of the respective configurations, functions, processing modules, processing means, and the like that have been described may be implemented by hardware, for example, may be designed as an integrated circuit, or may be implemented by software by a processor interpreting and executing programs for implementing the respective functions.

The information on the programs, tables, files, and the like for implementing the respective functions can be stored in a storage device such as a memory, a hard disk drive, or a solid state drive (SSD) or a recording medium such as an IC card, an SD card, or a DVD.

Further, control lines and information lines that are assumed to be necessary for the sake of description are described, but not all the control lines and information lines that are necessary in terms of implementation are described. It may be considered that almost all the components are connected to one another in actuality.

What is claimed is:

1. A data analysis apparatus, comprising a processor capable of accessing a storage device and executing program instructions to perform the method of:
   first acquisition processing of acquiring a group of learning input data, which is a set of learning input data that contains values of a plurality of first data items, from the storage device;
   first setting processing of setting a plurality of first hash functions by generating first hash tables, which are independent of one another;
   first calculation processing of substituting each learning input data of the group of learning input data acquired by the first acquisition processing in each of the plurality of first hash functions set by the first setting processing, to thereby calculate a plurality of first hash values corresponding to the values of the plurality of first data items for each of the plurality of first hash functions;
   first selection processing of selecting, for the group of learning input data and for each of the plurality of first hash functions, a specific first hash value that satisfies a predetermined statistical condition from among the plurality of first hash values, which have been calculated for each of the plurality of first hash functions by the first calculation processing;
   second setting processing of setting a second hash function by generating a second hash table;
   second calculation processing of substituting, for the group of learning input data, each specific first hash value, which has been selected for each of the plurality of first hash functions by the first selection processing, in the second hash function set by the second setting processing, to thereby calculate a plurality of second hash values;
   first generation processing of generating a learning feature vector that indicates features of the group of learning input data by aggregating the plurality of second hash values corresponding to respective specific first hash values and obtained as a result of the calculation by the second calculation processing;
   acquiring, in the first acquisition processing, training data, which is a set of values of any one of second data items among a plurality of second data items in a group of learning output data, the group of learning output data corresponding to respective learning input data and being a set of learning output data having values of the plurality of second data items;
   executing learning parameter calculation processing of calculating a learning parameter for outputting the training data from the group of learning input data using the learning feature vector generated by the first generation processing and the training data acquired by the first acquisition processing;
   executing first weighting processing of weighting each of the plurality of first hash values corresponding to the values of the plurality of first data items based on the values of the plurality of first data items for each learning input data;
   selecting, in the first selection processing, for the group of learning input data, a specific weighted first hash value that satisfies the predetermined statistical condition for each of the plurality of first hash functions from among the plurality of weighted first hash values obtained by the first weighting processing;
   calculating, in the second calculation processing, for the group of learning input data, the plurality of second hash values by substituting, in the second hash function, each specific weighted first hash value selected for each of the plurality of first hash functions by the first selection processing; and
   generating, in the first generation processing, the learning feature vector by aggregating, using odd-filtering, the plurality of second hash values corresponding to respective specific weighted first hash values and obtained as a result of the calculation by the second calculation processing.

2. The data analysis apparatus according to claim 1, wherein the processor is configured to generate, in the first generation processing, the learning feature vector by aggregating, using folding calculation, the plurality of second hash values corresponding to respective specific weighted first hash values and obtained as a result of the calculation by the second calculation processing.

3. The data analysis apparatus according to claim 1, wherein the processor is configured to calculate, in the learning parameter calculation processing, the learning parameter by substituting the learning feature vector and the training data in a classifier when the training data takes two values.

4. The data analysis apparatus according to claim 1, wherein the processor is configured to calculate, in the learning parameter calculation processing, the learning parameter by substituting the learning feature vector and the training data in a regression function when the training data takes one of multiple values and real values.

5. The data analysis apparatus according to claim 1, wherein the processor is configured to:
   execute cross-validation processing using the group of learning input data and a group of learning output data, which is a set of learning output data having a plurality of second data items, until execution of the first generation processing after execution of the second calculation processing;
   re-execute the first setting processing, the first calculation processing, the first selection processing, the second setting processing, and the second calculation processing until a prediction accuracy obtained by the cross-validation processing exceeds a threshold value; and
   execute the first generation processing when the prediction accuracy obtained by the cross-validation processing exceeds the threshold value, and
   wherein, in the cross-validation processing, the processor is configured to:
   calculate a first learning parameter for outputting first training data from a first group of learning input data among the group of learning input data using the first group of learning input data and the first training data, the first training data being a set of values of any one of second data items in a first group of learning output data corresponding to the first group of learning input data among the group of learning output data;
   calculate prediction data on the any one of second data items using second learning input data other than the first group of learning input data among the group of learning input data and the first learning parameter;
   calculate the prediction accuracy relating to the prediction data by comparing the prediction data with second training data, which is a set of values of the any one of second data items in a second group of learning output data corresponding to a second group of learning input data among the group of learning output data; and
   determine whether or not the prediction accuracy is equal to or smaller than the threshold value.

6. The data analysis apparatus according to claim 1, wherein the processor is configured to execute:
   second acquisition processing of acquiring a group of prediction input data, which is a set of prediction input data that contains values of the plurality of first data items, from the storage device;
   third calculation processing of substituting each prediction input data of the group of prediction input data acquired by the second acquisition processing in each of the plurality of first hash functions, to thereby calculate a plurality of third hash values corresponding to the values of the plurality of first data items for each of the plurality of first hash functions;
   second selection processing of selecting, for the group of prediction input data and for each of the plurality of first hash functions, a specific third hash value that satisfies a predetermined statistical condition from among the plurality of third hash values, which have been calculated for each of the plurality of first hash functions by the third calculation processing;
   fourth calculation processing of substituting, for the group of prediction input data, each specific third hash value, which has been selected for each of the plurality of first hash functions by the second selection processing, in the second hash function, to thereby calculate a plurality of fourth hash values; and
   second generation processing of generating a prediction feature vector that indicates features of the group of prediction input data by aggregating the plurality of fourth hash values corresponding to respective specific third hash values and obtained as a result of the calculation by the fourth calculation processing.

7. The data analysis apparatus according to claim 6, wherein the processor is configured to:
   execute second weighting processing of weighting each of the plurality of first hash values corresponding to the values of the plurality of first data items based on the values of the plurality of first data items for each prediction input data;
   select, in the second selection processing, for the group of prediction input data, a specific weighted third hash value that satisfies the predetermined statistical condition for each of the plurality of first hash functions from among the plurality of weighted third hash values obtained by the second weighting processing;
   calculate, in the fourth calculation processing, for the group of prediction input data, the plurality of fourth hash values by substituting, in the second hash function, each specific weighted third hash value selected for each of the plurality of first hash functions by the second selection processing; and
   generate, in the second generation processing, the prediction feature vector by aggregating, using odd-filtering, the plurality of fourth hash values corresponding to respective specific weighted third hash values and obtained as a result of the calculation by the fourth calculation processing.

8. The data analysis apparatus according to claim 6, wherein the processor is configured to generate, in the second generation processing, the prediction feature vector by aggregating, using folding calculation, the plurality of fourth hash values corresponding to respective specific weighted third hash values and obtained as a result of the calculation by the fourth calculation processing.

9. The data analysis apparatus according to claim 6, wherein the processor is configured to execute prediction value calculation processing of calculating a prediction value on the any one of second data items using the prediction feature vector generated by the second generation processing and the learning parameter.

10. The data analysis apparatus according to claim 9, wherein the processor is configured to calculate, in the prediction value calculation processing, the prediction value on the any one of second data items by substituting the prediction feature vector generated by the second generation processing and the learning parameter in a classifier when the training data takes two values.

11. The data analysis apparatus according to claim 9, wherein the processor is configured to calculate, in the prediction value calculation processing, the prediction value on the any one of second data items by substituting the prediction feature vector generated by the second generation processing and the learning parameter in a regression function when the training data takes one of multiple values and real values.

12. A data analysis method, which is executed by a processor capable of accessing a storage device, the data analysis method comprising executing, by the processor:
   first acquisition processing of acquiring a group of learning input data, which is a set of learning input data that contains values of a plurality of first data items, from the storage device;

first setting processing of setting a plurality of first hash functions by generating first hash tables, which are independent of one another;

first calculation processing of substituting each learning input data of the group of learning input data acquired by the first acquisition processing in each of the plurality of first hash functions set by the first setting processing, to thereby calculate a plurality of first hash values corresponding to the values of the plurality of first data items for each of the plurality of first hash functions;

first selection processing of selecting, for the group of learning input data and for each of the plurality of first hash functions, a specific first hash value that satisfies a predetermined statistical condition from among the plurality of first hash values, which have been calculated for each of the plurality of first hash functions by the first calculation processing;

second setting processing of setting a second hash function by generating a second hash table;

second calculation processing of substituting, for the group of learning input data, each specific first hash value, which has been selected for each of the plurality of first hash functions by the first selection processing, in the second hash function set by the second setting processing, to thereby calculate a plurality of second hash values;

first generation processing of generating a learning feature vector that indicates features of the group of learning input data by aggregating the plurality of second has h values corresponding to respective specific first hash values and obtained as a result of the calculation by the second calculation processing;

acquiring, in the first acquisition processing, training data, which is a set of values of any one of second data items among a plurality of second data items in a group of learning output data, the group of learning output data corresponding to respective learning input data and being a set of learning output data having values of the plurality of second data items;

executing learning parameter calculation processing of calculating a learning parameter for outputting the training data from the group of learning input data using the learning feature vector generated by the first generation processing and the training data acquired by the first acquisition processing;

executing first weighting processing of weighting each of the plurality of first hash values corresponding to the values of the plurality of first data items based on the values of the plurality of first data items for each learning input data;

selecting, in the first selection processing, for the group of learning input data, a specific weighted first hash value that satisfies the predetermined statistical condition for each of the plurality of first hash functions from among the plurality of weighted first hash values obtained by the first weighting processing;

calculating, in the second calculation processing, for the group of learning input data, the plurality of second hash values by substituting, in the second hash function, each specific weighted first hash value selected for each of the plurality of first hash functions by the first selection processing; and generating, in the first generation processing, the learning feature vector by aggregating, using odd-filtering, the plurality of second hash values corresponding to respective specific weighted first hash values and obtained as a result of the calculation by the second calculation processing.

13. A non-transitory recording medium having stored thereon a program to be executed by a processor capable of accessing a storage device, the non-transitory recording medium being readable by the processor, the non-transitory recording medium having recorded thereon a data analysis program for causing the processor to execute:

first acquisition processing of acquiring a group of learning input data, which is a set of learning input data that contains values of a plurality of first data items, from the storage device;

first setting processing of setting a plurality of first hash functions by generating first hash tables, which are independent of one another;

first calculation processing of substituting each learning input data of the group of learning input data acquired by the first acquisition processing in each of the plurality of first hash functions set by the first setting processing, to thereby calculate a plurality of first hash values corresponding to the values of the plurality of first data items for each of the plurality of first hash functions;

first selection processing of selecting, for the group of learning input data and for each of the plurality of first hash functions, a specific first hash value that satisfies a predetermined statistical condition from among the plurality of first hash values, which have been calculated for each of the plurality of first hash functions by the first calculation processing;

second setting processing of setting a second hash function by generating a second hash table;

second calculation processing of substituting, for the group of learning input data, each specific first hash value, which has been selected for each of the plurality of first hash functions by the first selection processing, in the second hash function set by the second setting processing, to thereby calculate a plurality of second hash values;

first generation processing of generating a learning feature vector that indicates features of the group of learning input data by aggregating the plurality of second hash values corresponding to respective specific first hash values and obtained as a result of the calculation by the second calculation processing;

acquiring, in the first acquisition processing, training data, which is a set of values of any one of second data items among a plurality of second data items in a group of learning output data, the group of learning output data corresponding to respective learning input data and being a set of learning output data having values of the plurality of second data items;

executing learning parameter calculation processing of calculating a learning parameter for outputting the training data from the group of learning input data using the learning feature vector generated by the first generation processing and the training data acquired by the first acquisition processing;

executing first weighting processing of weighting each of the plurality of first hash values corresponding to the values of the plurality of first data items based on the values of the plurality of first data items for each learning input data;

selecting, in the first selection processing, for the group of learning input data, a specific weighted first hash value that satisfies the predetermined statistical condition for each of the plurality of first hash functions from among the plurality of weighted first hash values obtained by the first weighting processing;

calculating, in the second calculation processing, for the group of learning input data, the plurality of second hash values by substituting, in the second hash function, each specific weighted first hash value selected for each of the plurality of first hash functions by the first selection processing; and generating, in the first generation processing, the learning feature vector by aggregating, using odd-filtering, the plurality of second hash values corresponding to respective specific weighted first hash values and obtained as a result of the calculation by the second calculation processing.

* * * * *